(12) United States Patent
Finkelstein et al.

(10) Patent No.: US 6,283,923 B1
(45) Date of Patent: Sep. 4, 2001

(54) SYSTEM AND METHOD FOR REMOTELY MONITORING ASTHMA SEVERITY

(75) Inventors: Joseph Finkelstein; George Hripcsak, both of New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/089,577

(22) Filed: Jun. 3, 1998

Related U.S. Application Data

(63) Continuation-in-part of application No. 09/086,165, filed on May 28, 1998, now abandoned.

(51) Int. Cl.[7] .................................................. A61B 5/08
(52) U.S. Cl. .......................... 600/532; 600/300; 600/538; 128/503; 128/904
(58) Field of Search ................................... 600/529, 532, 600/534, 538, 300; 128/903, 904

(56) References Cited

U.S. PATENT DOCUMENTS

| | | | |
|---|---|---|---|
| 3,737,863 | 6/1973 | Rowland et al. | 340/172.5 |
| 4,250,890 | 2/1981 | Jones et all. | 128/728 |

(List continued on next page.)

OTHER PUBLICATIONS

K.B. Weiss, P.J. Gergen and T.A. Hodgson, "An Economic Evaluation of Asthma in the United States," *New England Journal of Medicine.*, vol. 36, pp. 862–866 (1992).

E.R. McFadden, R. Kiser and W.J. DeGroot, "Acute Bronchial Asthma: Relations Between Clinical and Physiological Manifestations," *New England Journal of Medicine*, vol. 288, pp. 221–225 (1973).

A.R. Rubinfeld, "Pain MCF: Perception of Asthma," *The Lancet*, pp. 882–884 (1976).

"Li JTC Home Peak Expiratory Flow Rate Monitoring in Patients With Asthma," *Mayo Clin. Proc.*, vol. 70, pp. 649–656 (1995).

R. Beasley, M. Cushley and S.T. Holgate, "Self–Management Plan in the Treatment of Adult Asthma," *Thorax*, vol. 4, pp. 200–204 (1989).

(List continued on next page.)

*Primary Examiner*—Robert L. Nasser
(74) *Attorney, Agent, or Firm*—Baker Botts LLP

(57) ABSTRACT

A system for remotely monitoring asthma severity includes a remotely located asthma monitoring station for administering a patient self-test and for gathering test data and relevant patient information indicative of asthmatic symptoms, and a central processing facility for receiving the test data and patient information from the remote monitoring station, determining whether the test data is valid, analyzing valid test data to generate test results and an appropriate response message to the monitoring station, storing the test results in a central data repository, and disseminating the test results and response message in a timely manner as required. The monitoring system also includes a remotely located diagnosis/evaluation station for displaying the test results, response messages and other patient information. Selectable data links are provided for real-time reciprocal exchange of the test data, test results, response message and patient information between said monitoring station, said central processing facility and said diagnosis/evaluation station. Preferably, the remote monitoring station, central processing facility and remote diagnosis/evaluation station are connected via the Internet wherein the test results can be accessed via a conventional Web browser.

19 Claims, 5 Drawing Sheets

Microfiche Appendix Included
(2 Microfiche, 96 Pages)

U.S. PATENT DOCUMENTS

| | | | |
|---|---|---|---|
| 4,852,582 | | 8/1989 | Pell .................................... 128/716 |
| 5,361,755 | | 11/1994 | Schraag et al. ..................... 128/630 |
| 5,373,851 | * | 12/1994 | Reinhold, Jr. et al. ............. 500/529 |
| 5,410,471 | * | 4/1995 | Alyfuku et al. .................... 600/300 |
| 5,492,117 | * | 2/1996 | Eisenberg et al. .................. 600/300 |
| 5,494,051 | | 2/1996 | Schneider, Sr. ..................... 128/870 |
| 5,518,002 | * | 5/1996 | Wolf et al. .......................... 600/538 |
| 5,553,609 | | 9/1996 | Chen et al. .......................... 128/630 |
| 5,704,366 | * | 1/1998 | Tacklind et al. .................... 600/538 |
| 5,911,132 | * | 6/1999 | Sloane ................................ 600/300 |

OTHER PUBLICATIONS

A.C. Ferguson, "Persistent Airway Obstruction in Asymptomatic Children With Asthma With Normal Peak Expiratory Flow Rates," *J. Allergy Clinical Immunology*, vol. 82, pp. 19–22 (1988).

C.H. Chiang and K. Hsu, "Residual Abnormalities of Pulmonary Function in Asymptomatic Young Adults Asthmatics with Childhood–Onset Asthma," *J. Asthma*, vol. 34, pp. 15–21, (1997).

R.E. Hyatt and L.F. Black, "The Flow Volume Curve," *Am. Rev. Rsp. Dis.*, vol. 107, pp. 191–199 (1973).

J.J. Cimino, S.B. Johnson, G. Hripscak, C.L. Hill and P.D. Clayton, "Managing Vocabulary for a Centralized Clinical System," *Medinfo*, vol. 8, pt 1, pp. 117–120 (1995).

\* cited by examiner

SYSTEM AND METHOD FOR REMOTELY MONITORING ASTHMA SEVERITY

This is a continuation-in-part of copending application Serial No. 09/086,165, filed May 28, 1998, now abandoned.

A portion of the disclosure of this patent document contains material which is subject to copyright protection. The copyright owner has no objection to the facsimile reproduction by anyone of the patent document or the patent disclosure, as it appears in the Patent & Trademark Office file or records, but otherwise reserves all copyright rights whatsoever.

A microfiche appendix containing source code listing utilizing an exemplary embodiment of the invention is included as part of the Specification and is hereinafter referred to as Appendix I. Appendix I includes 2 microfiche with 96 frames.

FIELD OF THE INVENTION

The present invention relates in general to the field of remote monitoring and diagnosing asthma and related symptoms. More particularly, the present invention relates to a system and method for remotely monitoring asthma severity in real-time via wireless and landline communications systems.

BACKGROUND OF THE INVENTION

Approximately 15 million Americans suffer in varying degrees from different forms of asthma. In 1990 alone, nearly 6.2 billion dollars were spent in total in the United States on asthma-related costs. Approximately 2 billion dollars of this amount were spent on in-patient hospital and emergency room services, and approximately 2.6 billion dollars on indirect costs such as loss of work, child care and premature death. See K. B. Weiss, P. J. Gergen and T. A. Hodgson, "An Economic Evaluation of Asthma in the United States," *New Eng. J. Med.*, vol. 326, pp. 862–866 (1992). Despite advances in the treatment of asthma, the morbidity and mortality of the disease has increased significantly during the past several years. Moreover, asthma continues to present significant management problems for patients trying to cope with the disease on a day-to-day basis and for physicians providing medical care and treatment.

A common problem in assessing the severity of asthmatic symptoms is that patients frequently misperceive and underestimate the severity of airway obstruction. See E. R. McFadden, R. Kiser and W. J. De Groot, "Acute Bronchial Asthma: Relations Between Clinical and Physiological Manifestations," *New Eng. J. Med.*, vol. 288, pp. 221–225 (1973); A. R. Rubinfeld, "Pain MCF: Perception of Asthma," *The Lancet*, pp. 882–884 (1976). Consequently, in-home monitoring of asthmatic symptoms, combined with patient education, has been shown to significantly reduce the incidence of asthma exacerbation and subsequent hospitalization. See "Li JTC. Home Peak Expiratory Flow Rate Monitoring in Patients With Asthma.," *Mayo Clin. Proc.*, vol. 70, pp. 649–656 (1995).

In-home monitoring of asthma severity is especially useful for detecting diminished lung function before serious respiratory symptoms become evident. See R. Beasley, M. Cushley and S. T. Holgate, "A Self-Management Plan in the Treatment of Adult Asthma," *Thorax*, vol. 4, pp. 200–204 (1989). By identifying diminished lung function before clinical symptoms develop, a patient or physician may intervene so as to prevent worsening of a condition which may otherwise result in hospitalization or death. As such, the Expert Panel of National Asthma Education and Prevention Program considers ongoing monitoring of pulmonary function as an essential part of asthma management.

Although effective for managing and treating asthma, the reliability and accuracy of conventional in-home monitoring systems are limited by several factors. First, conventional in-home monitoring systems do not allow physicians to review and assess test results in a timely manner. Even the most advanced conventional systems, which gather peak flow data, only allow physicians to download and review patient data on a monthly or weekly basis. Still others allow patients to fax peak flow data used to generate reports that are reviewed monthly by the physician. Conventional in-home monitoring systems do not allow the timely and reciprocal exchange of patient data and medical advice between the physician and the patient, and provide no means for notifying the physician or patient of any changes in peak flow trends that occur between scheduled reports. As such, if an ominous trend or asthma exacerbation occurs between downloads or other information exchange, conventional in-home monitoring systems do not allow physicians to recognize potential problems or intervene until after the monthly or other periodic report has been generated and reviewed.

Second, conventional in-home monitoring systems completely rely on the patient's ability to properly perform and document the tests. Conventional systems do not provide automated tools for assessing the patient's compliance, and do not provide capabilities for providing meaningful reciprocal data exchange between the patient and the physician as the test is being performed.

Third, conventional systems use simple, unsophisticated and frequently inaccurate methods for evaluating the severity of asthmatic symptoms. For example, conventional systems rely on peak expiratory flow ("PEF") measurements to evaluate asthma severity. Although easy to administer, the accuracy of PEF tests can vary largely from patient to patient. This is so because the accuracy of the PEF measurements depend largely upon the patient's effort and the strength of his' or hers' expiratory muscles. In fact, several studies have shown the presence of persistent airway obstructions in asymptotic children and adults having seemingly normal PEF'S. See A. C. Ferguson, "Persistent Airway Obstruction in Asymptomatic Children With Asthma With Normal Peak Expiratory Flow Rates," *J. Allergy Clinical Immunology*, vol. 82, pp. 19–22 (1988); C. H. Chiang and K. Hsu, "Residual Abnormalities of Pulmonary Function in Asymptomatic Young Adults Asthmatics with Childhood-Onset Asthma," *J. Asthma*, vol. 34, pp. 15–21, (1997).

By contrast, the Forced Vital Capacity test ("FVC"), which requires sophisticated computerized analysis, has been shown to be a more precise test for evaluating asthma severity. The FVC test is also better than PEF tests for assessing the degree of small airways resistance. See R. E. Hyatt and L. F. Black, "The Flow Volume Curve," *Am. Rev. Resp. Dis.*, vol. 107, pp. 191–199 (1973). In short, the same study also concluded that FVC tests provide the most reliable assessment of airway dysfunction in asthmatics. See id.

And lastly, conventional in-home monitoring systems do not provide computerized clinical decision support tools for processing and evaluating test data, thus leaving physicians with voluminous data which is very difficult to analyze in a timely and effective manner. Moreover, conventional in-home monitoring systems do not provide means for alerting the patient, in a real-time manner, of potentially serious respiratory conditions the may require immediate treatment and/or hospitalization.

As such, asthma continues to present significant management problems for patients attempting to cope with the disease on a day-to-day basis and for the physicians guiding and advising them. For the reasons noted above, conventional in-home monitoring systems and methods are limited and remain largely inadequate.

SUMMARY OF THE INVENTION

The aforedescribed limitations and inadequacies of conventional asthma monitoring techniques are substantially overcome by the present invention, which in a preferred embodiment is a system for monitoring asthma that includes: a remotely located asthma monitoring station for administering a patient self-test and for gathering test data and relevant patient information indicative of asthmatic symptoms; a central processing facility for receiving the test data and patient information from the monitoring station, processing the test data to determine whether the test data is valid, analyzing valid test data to generate test results and an appropriate response message to the monitoring station, storing the test results in a central data repository, and disseminating the test results and response message in a timely manner as required; and a remotely located diagnosis/evaluation station for displaying the test results, response message and patient information. Selectable data links are provided for real-time reciprocal exchange of the test data, test results, response message and patient information between the monitoring station, the central processing facility and the diagnosis/evaluation station.

Advantageously, the remote monitoring station, central processing facility and remote diagnosis/evaluation station are connected via the Internet and test results are readily accessible from the central processing facility via a conventional Web browser. In addition, a wireless data link between the remote monitoring station and the central processing facility is preferred for the convenience and mobility of the patient.

In accordance with another aspect of the invention, a method is provided for monitoring asthma severity. The method includes the steps of administering a self-test at a remotely located monitoring station to gather test data and relevant patient information indicative of asthmatic symptoms (or the lack thereof), transmitting the test data and patient information from the monitoring station to a central processing facility, processing the test data by the central processing facility to determine whether the test data is valid, analyzing valid test data to generate test results and an appropriate response message, storing the test results in a central data repository, disseminating the test results and response message in a timely manner as required, and displaying the test results, response message and patient information at a remotely located diagnosis/evaluation station.

In accordance with yet another aspect of the invention, a computer program is provided for use with a system for remotely monitoring asthma severity. The computer program requires at least one remotely located computer usable medium, at least one centrally located computer usable medium, and distributed computer readable program code means embodied in the remotely and centrally located computer usable media. The program code means provides for administering a self-test at a remotely located monitoring station to gather test data and relevant patient information indicative of asthmatic symptoms; transmitting the test data and patient information from the monitoring station to a central processing facility; processing the test data by the central processing facility to determine whether the test data is valid; analyzing valid test data to generate test results and an appropriate response message; storing the test results in a central data repository; disseminating the test results and the response message in a timely manner as required; and displaying the test results, response message and patient information at a remotely located diagnosis/evaluation station.

BRIEF DESCRIPTION OF THE DRAWINGS

For a complete understanding of the present invention and the advantages thereof, reference is now made to the following description taken in conjunction with the accompanying drawings in which like reference numbers indicate like features and wherein.

DETAILED DESCRIPTION OF THE INVENTION

Figure 1:
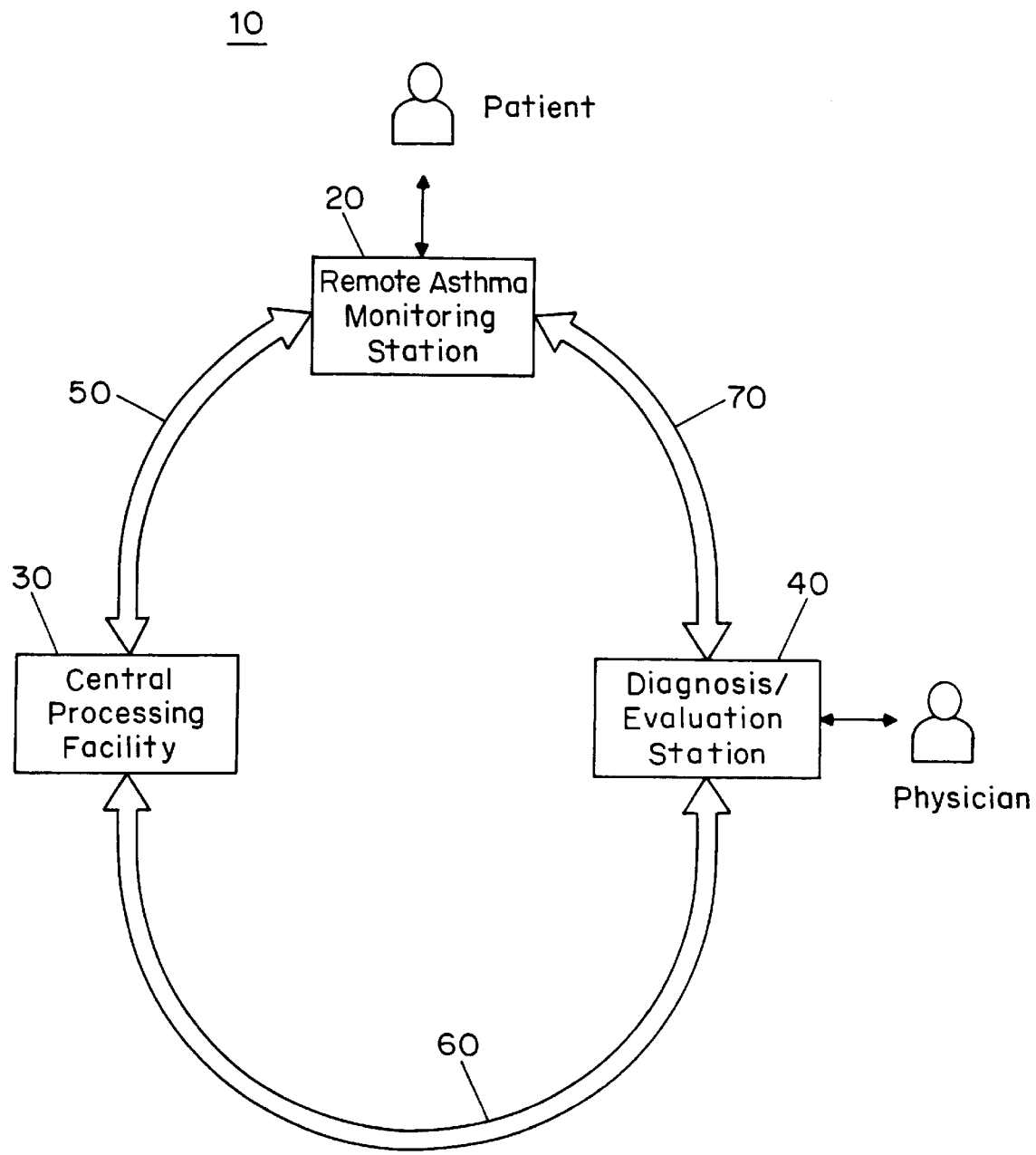
FIG. 1 shows block diagram of a system for remotely monitoring asthma severity according to a preferred embodiment of the present invention.

FIG. 1 is a block diagram of a system 10 for remotely monitoring asthma severity. The monitoring system 10 comprises at least one remotely located asthma monitoring station 20 (only one shown), a central processing facility 30, and at least one diagnosis/evaluation station 40 (only one shown). Via selectable data links 50, 60 and 70, a physician is able to remotely monitor, in real-time, a patient's asthmatic symptoms and intervene if warranted by the severity of the patient's condition.

Each monitoring station 20 of the present embodiment is provided with a graphical user interface ("GUI"), which a patient uses to provide relevant patient information and to administer a self-test to assess asthma severity. Test data is collected by the monitoring station 20 and transmitted via a first selectable data link 50 to the central processing facility 30. The data link 50 can be established via any public or proprietary wireless or landline communication system.

Test data transmitted via the first selectable data link 50 is then received by the central processing facility 30 for processing and evaluation. If the test data is determined to be valid, thus indicating that the self-test was properly administered, the data is analyzed and stored in a central data repository (not shown) located at the central processing facility 30. Test results are generated, along with an appropriate response message or instruction, and disseminated in a timely manner via selectable data links 50 and 60 to the physician at the diagnosis/evaluation station 40 and/or the patient at the remote monitoring station 20. If the central processing facility 30 determines for some reason that the test data is invalid, the central processing facility 30 discards the data and issues a request response message to the remote monitoring station 20 via the first data link 50 instructing the patient to repeat the self-test at the remote monitoring station 20.

Like the remote monitoring station 20, the diagnosis/evaluation station 40 is provided with a GUI which allows the physician to display, review and further evaluate the test results received from the central processing facility 30. From the diagnosis/evaluation station 40, the physician is further able to intervene via data links 60 and 70 if necessitated by the severity of the patient's condition. As with the data link 50, data links 60 and 70 can be established via any public or proprietary wireless or landline communications system.

Figure 2:
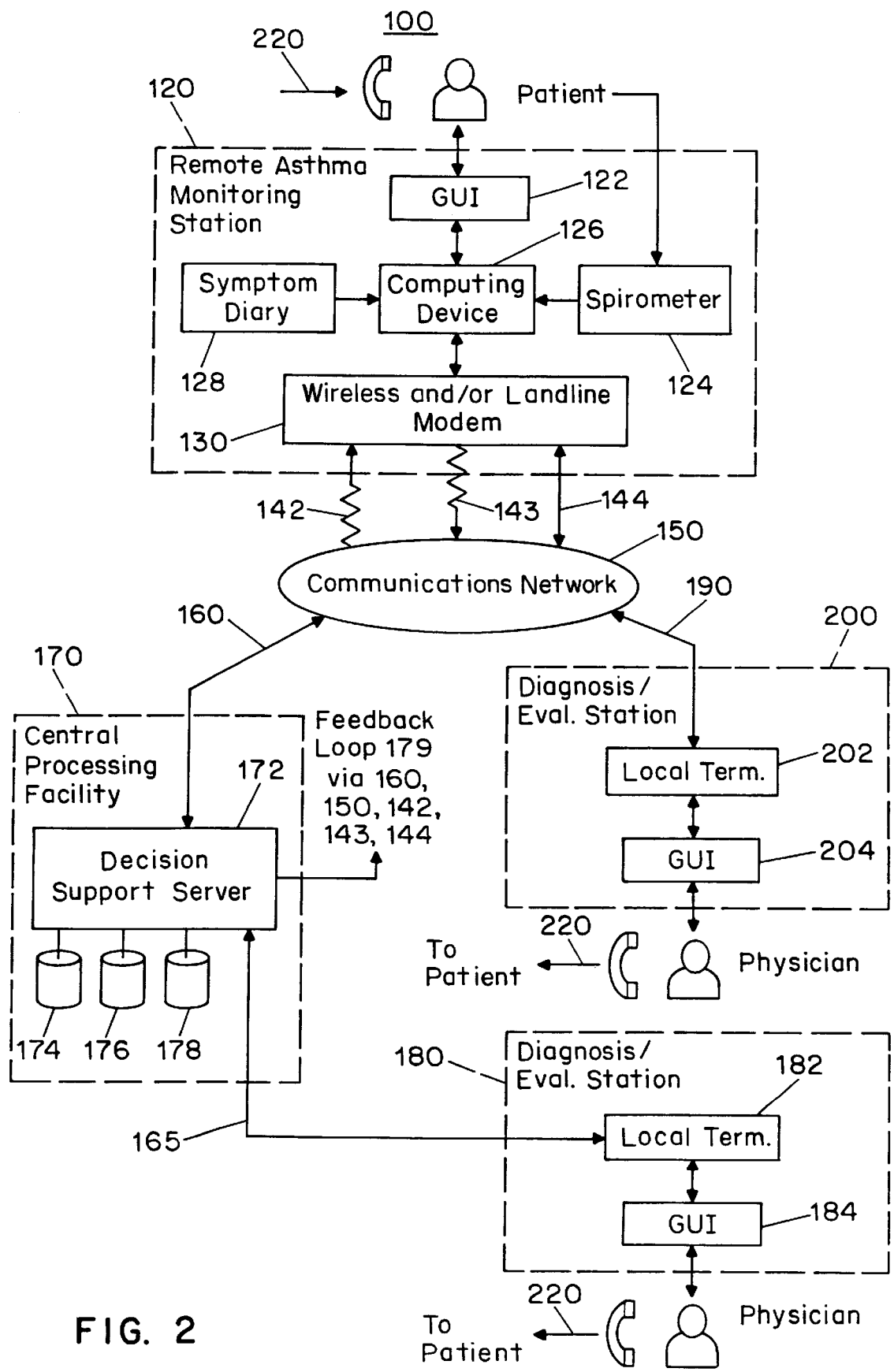
FIG. 2 shows another preferred embodiment of a system for remotely monitoring asthma severity.

FIG. 2 shows a second preferred embodiment of a system for monitoring asthma severity. The system 100 includes at least one remotely located asthma monitoring station 120 linked via a wireless or landline data link 140,142, or 144 to a communications network 150. Preferably, the communications network 150 is the Internet, but can also be any local area network ("LAN"), wide area network ("WAN") or other computer network providing a suitable messaging service.

The communications network 150 is further linked to a central processing facility 170, a local diagnosis/evaluation station 180, and a remotely located diagnosis/evaluation station 200 via landline data links 160, 165 and 190, respectively. The central processing facility 170 can be part of any hospital or medical information system. Physicians at the diagnosis/evaluation stations 180 and 200 are linked back to the central processing facility 170 and/or the remote monitoring station 120 via the appropriate selectable data link. In addition, physicians can link directly to the patient, e.g., via voice, via cellular phone or landline telephone networks 220.

As shown in FIG. 2, the remote monitoring station 120 includes a spirometer 124 for performing a forced vitality capacity test as part of the patient self-test, a computing device 126 for reciprocal data exchange with the central processing facility 170, a patient GUI 122 for interfacing between the patient and the computing device 126, and a symptom diary 128 for storing data related to questions regarding relevant patient information and patient responses to those questions, and a wireless and/or landline modem 130 for communicating with the communications network 150. Preferably, the spirometer 124 is a portable handheld device such as the Vitalograph V2120 which is connected to the computing device 126 via a serial port or other compatible interface. The patient GUI 122, which the patient uses to answer questions provided by the symptom diary and to perform the self-test, is designed to have a minimal number of selectable options and error messaging capabilities to indicate operator error or equipment failure.

The computing device 126, preferably a battery-operated palmtop computer such as a Hewlett Packard HP200LX or a Prolinear MiniNote PS-300, includes PCMCIA slots or other network compatible interfaces and includes or is connected to a wireless and/or landline modem 130. Preferably, the computing device 126 also includes on-board flash memory with an installation copy the software required to perform the required remote monitoring functions.

Although a wireless system is preferred for convenience and mobility, e.g., the Cellular Digital Packet Data network ("CDPD"), the RAM Mobile network, etc., standard telephone lines can be used to link the remote monitoring station 120 to the communications network 150. The following modems, for example, are recommended: PCMCIA modem (landline modem); Motorola PM100C modem (CDPD modem); and Megahertz AllPoints wireless modem (RAM Mobile network modem). Data transfer over the landline modem is based on direct dial-up connection with the central processing facility 170. Data transfer based on the CDPD modem uses the Telnet protocol, and data transfer over the RAM Mobile network is based on e-mail exchange with the central processing facility 170. Regardless of the modem used, the computing device 126 is capable of automatically recognizing the modem type to allow seamless transfer of information between landline and wireless communications systems.

The computing device 126 of FIG. 2 performs several functions, including but not limited to collecting relevant information from the patient for the symptom diary 128, collecting FVC test results from the spirometer 124, performing initial error detection with respect to the FVC test results, connecting to the communications network 150, and automatically forwarding the test results via the wireless modem 130 to the central processing facility 170. In addition, the computing device 126 provides reciprocal exchange of information between the patient and the physician in the form of messages, alerts and reminders, and periodically downloads software upgrades from the central processing facility 170.

With the aforementioned remote monitoring station 120, patients are asked to perform self-tests twice a day in the morning and evening before and after the use of a bronchodilator. The asthma measurement comprises a FVC test and a symptom diary. The computer allows patients to promptly evaluate the severity of their asthma symptoms using visual scales, and then patients perform the FVC test. After completion of self-testing, the data is immediately transmitted to the decision support server 172 at the central processing facility 170. Shortly after completion of the self-test, the patient receives an acknowledgment message from the decision support server 172. However, If a connection cannot be established with the decision support server 172, the test data is stored locally at the remote monitoring station 120 and transmitted during the next successful communication session.

Also, in event that the computing device 126 is unable to connect to the central processing facility 170 as shown in FIG. 2, the computing device 126 is capable of implementing a PEF test per guidelines established by the National Heart, Lung and Blood Institute ("NHLBI"). These guidelines provide an approximate classification of asthma severity into three categories: good control, caution, medical alert. Thus, as a back-up mode of operation, the computing device 126 is capable of notifying the patient about a serious respiratory condition regardless of remote connectivity to the rest of the system.

Test data collected by the computing device 126 is transmitted to the central processing facility 170 immediately upon completion of the patient self-test. The central processing facility 170 comprises a decision support server 172, a central data repository 124 for storing valid test data, and one or more databases 176 and 178, e.g., the Medical Entities Dictionary ("MED"), International Classification of Diseases version 9 ("ICD-9") databases, Unified Medical Language System ("UMLS"), etc., for analysis and support purposes. Preferably, the decision support server 172 is a UNIX host and the central processing facility 170 is connected to the communications network 150 via a landline data link 160.

After test data is received by the central processing facility 170 from the monitoring station 120, the decision support server 172 first checks the validity of the test data against pre-determined limits to determine whether the self-test was properly administered. If the test data is valid, the decision support server 170 transmits a confirmation message back to the monitoring station 120 via a decision feedback loop 179. If however, the test data is determined to be invalid or corrupted, an immediate request message is transmitted back to the monitoring station 120 requesting the patient to re-administer the self-test. Preferably, the immediate request message is forwarded as an e-mail message to a Web page to which the patient has accessed.

After the decision support server 172 determines that it has received valid test data, the decision support server 172 evokes algorithms to analyze and evaluate the test data. The data is analyzed to determine whether there are any trends, and to generate the appropriate messages, alarms or reminders to the patient or physician. Absolute values and parameter trends are analyzed by the decision support server 172 according to standards and guidelines established by NHLBI. Test results are then automatically stored in a central data repository 174, preferably using HL7 message formats according to MED vocabulary codes. See J. J. Cimino, S. B. Johnson, G. Hripcsak, C. L. Hill & P. D. Clayton, "Managing Vocabulary for a Centralized Clinical System," *Medinfo*, vol. 8, pt 1, pp. 117–120 (1995). The central data repository 174 is preferably a relational database such as IBM's DB2.

Each time the central processing facility 170 receives new data, the decision support server 172 retrieves the previous test results and analyzes the test data to check whether pre-defined alert conditions are satisfied. If alert conditions are satisfied, the system automatically sends an immediate alert message to the patient and/or physician advising the patient to immediately consult with the physician or to follow a pre-defined exacerbation treatment plan. Preferably, the alert message is also forwarded as an e-mail message to a Web page which the patient has accessed.

Alert parameters can be preset for any of the twenty-nine FVC test parameters, and may be based on percent predicted or changes from previous values. Alerts may also be automatically set to default settings corresponding to the NHLBI guidelines. Alert conditions can be dynamically modified for any combination of parameters on the designated Web page according to the physician's treatment plan for a particular patient. New thresholds for decision support, provided by the computing device 126, can be downloaded from the decision support server 172 during subsequent communication sessions. In addition, the system periodically checks patient's compliance and generates alerts if the patient has failed to transmit a test within a predetermined period of time.

Otherwise, if no alert conditions are detected, the test results are automatically forwarded to the diagnosis/evaluation stations 180 and/or 200 for review by the physician(s) or other healthcare providers. A Common Gateway Interface ("cgi") program on the decision support server 172 allows physicians to review the test results directly from an Internet Web browser, and to analyze trends and compare previous and new results graphically using a superimposition of FVC curves. Absolute values and parameters trends may be analyzed according to the NHLBI guidelines. In addition, physician response messages can be sent back to the patient after the physician has reviewed the test results at the nearest diagnosis/evaluation station. Physician response messages are preferably sent via e-mail, and may for example notify the patient about future treatment changes or remind the patient to comply with a pre-defined asthma management plan.

After the analysis results are stored in the central data repository 174, the results become available for review at one or more diagnosis/evaluation stations 180 and 200. By way of example and not limitation, the monitoring system of FIG. 2 includes an internal diagnosis/evaluation station 180 connected directly to the central processing facility 170, and a remotely located diagnosis/evaluation station 200 connected to the central processing facility 170 via the communications network 150 and a landline pathway 190. As shown in FIG. 2, each of the diagnosis/evaluation stations 180 and 200 include a local terminal 182 and 202 and a physician interface 184 and 204. Preferably, the physician interface utilizes a commercially available Internet Web browser. In addition to viewing test results, a treating physician may also use the Web browser to forward messages regarding the test results to the patient's primary care physician. The treating physician can forward information indicating a significant deviation from normal parameters, and ask that a remotely located specialist review the test results and send recommendations using the same or compatible Web browser.

Figure 3:
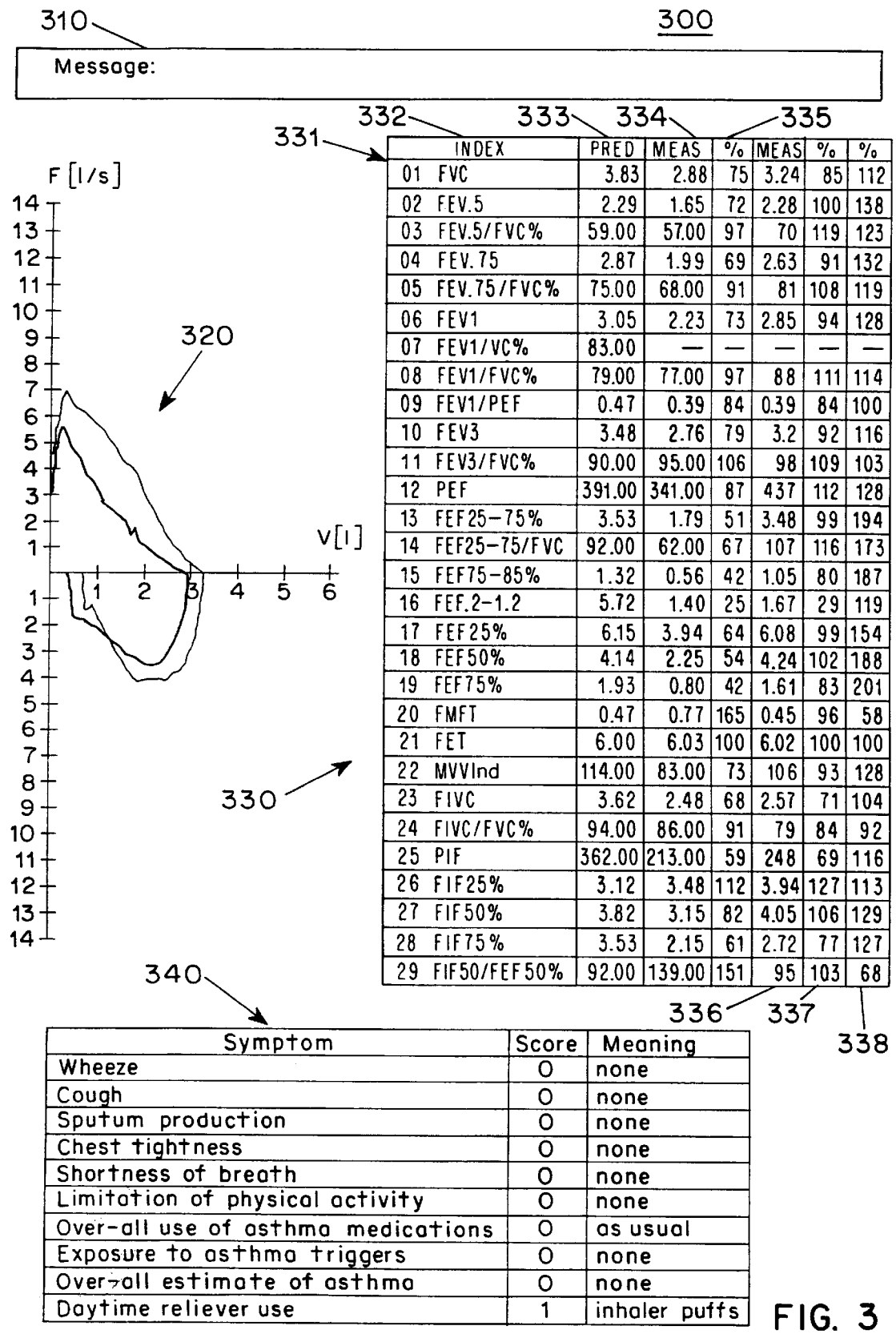
FIG. 3 is an example of a physician graphical user interface for use with the asthma monitoring system of FIG. 2.

FIG. 3 is an example of a GUI 300 corresponding to the physician interfaces 184 and 204 of FIG. 2. Via the GUI 300, preferably a Internet Webpage designed for use with any Netscape-compatible Web browser, a physician can choose for analysis purposes any test data set or any combinations of test data sets from a chronological list of performed tests. Each test data set is matched to the correct patient via a corresponding medical record number.

The GUI 300 as shown in FIG. 3 includes, but is not limited to, a message display region 310 for displaying messages received from a patient and for sending messages to the patient, a graphical display region 320 for displaying a graphical representation of flow-volume data, a region 330 for displaying a table of FVC test results, and a region 340 for displaying a symptom diary. Each region can be reconfigured, resized or rearranged on the GUI 300 as desired by the physician. Preferably, the message display region 310 is displayed after the region 340 on the GUI 300.

The graphical display region 320 of FIG. 3 provides a graphical representation of flow-volume data that is extremely useful for quickly assessing, diagnosing and treating potentially serious asthmatic symptoms. In the graphical display region 320, current FVC test results can be displayed superimposed against baseline test results for easy comparison.

The display region 330 is also helpful to the physician, and is used for displaying a table of selected FVC test parameters. As shown in FIG. 3, the table in the display region 330 shows a summary of the 29 FVC spirometric parameters derived from a single administration of an FVC self-test. These parameters characterize lung volumes and bronchial obstruction at different levels of the bronchial tree. Of the 29 parameters, PEF, Forced Expiratory Volume ("FEV1"), and Forced Mid-Expiratory Flow ("FEF25–75%") are generally considered to be the most important parameters in diagnosing asthma severity. PEF is the largest expiratory flow, which is achieved with a maximally forced effort from a position of maximal inspiration, and reflects bronchial obstruction mostly at the level of large airways. FEV1 is the volume of air exhaled during the first second of the FVC test, which declines proportionally to clinical worsening of airways obstruction. FEF25–75% is the mean expiratory flow during the middle half of the FVC, which has been shown to be indicative of bronchial obstruction of small airways, and is a strong indicator of asthma deterioration. Presently, there are no conventional monitoring systems that monitor the FEF25–75% parameter.

As further shown in FIG. 3, the table of display region 330 includes several columns from left to right indicating the following information: (1) the FVC index number (column 331), (2) the name of the corresponding FVC parameter (column 332), (3) the predicted value for that FVC parameter, i.e., the normal value that a person of the same gender, height and age should have (column 333), (4) the actual measured value for that FVC parameter (column 334), and (5) the percentage of the actual value as compared to the predicted value (column 335). If a physician chooses more than one test for analysis, the table provides comparison between two tests: the baseline (oldest test) and the current test. In such a case, columns are provided for displaying the percentage of the baseline values as compared to the predicted values (column 335), the actual measured values for the current test (column 336), the percentage of the current values as compared to the predicted values (column 337), and difference between the baseline and current values in percentages (column 338).

The GUI of FIG. 3 also includes a region 340 for a summary of symptoms representing answers provided by the patient in response to the symptom diary questions presented to the patient during self-testing. Each answer is graded according to a predetermined scale, usually from 0 to 3. For example, wheezing is graded as 0 (none, no wheezing), 1 (mild wheezing), 2 (moderate wheezing), or 3 (severe wheezing).

Figure 4:
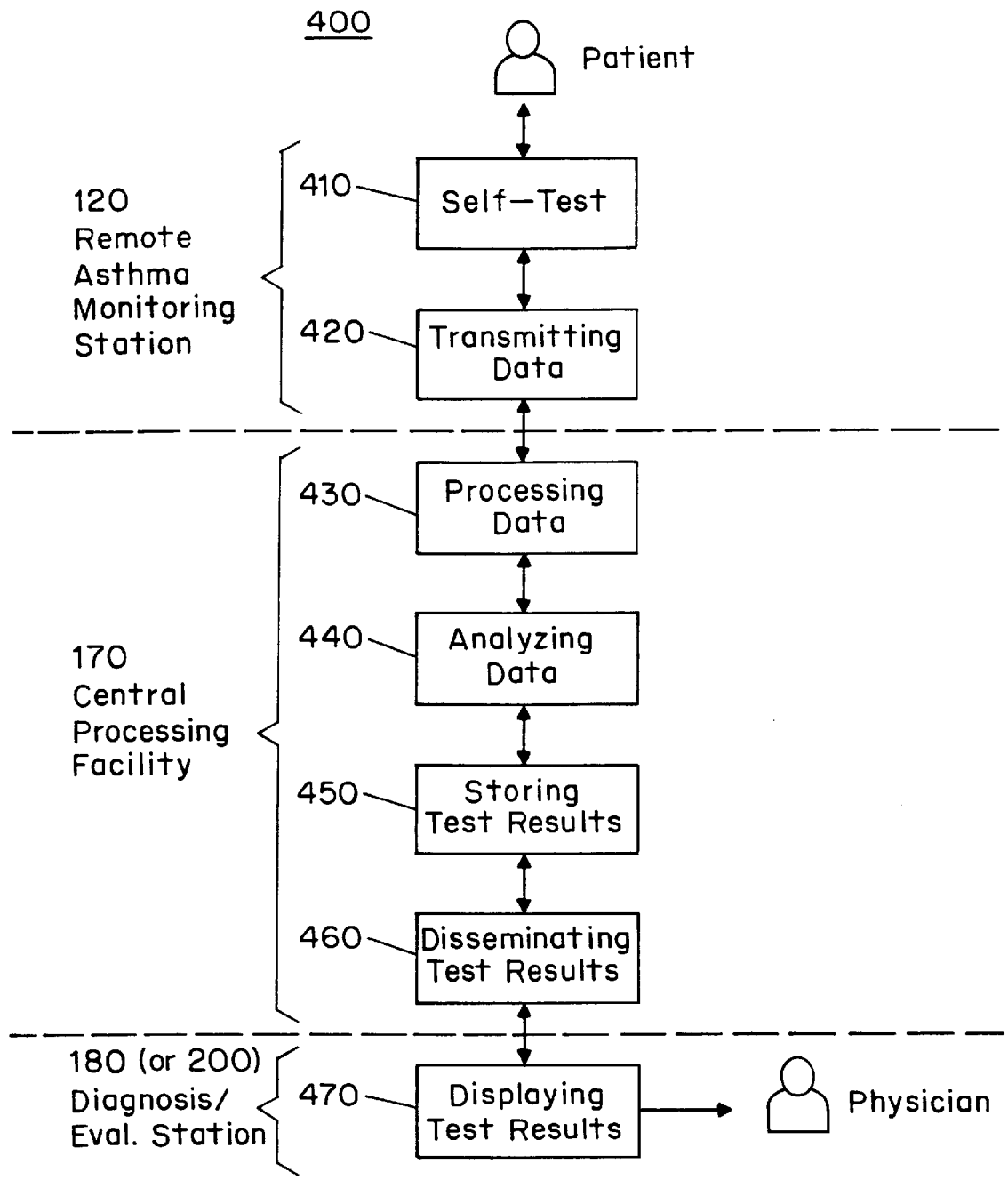
FIG. 4 is flow diagram showing a preferred method for remotely monitoring asthma severity.

FIG. 4 is a flow diagram showing a preferred method for monitoring asthma severity according to the present invention. The method 400 includes the steps of administering a self-test, e.g., using a spirometer and answering symptom diary questions, at a remotely located monitoring station to gather test data and relevant patient information indicative of asthmatic symptoms (Step 410) and transmitting the test data and patient information from the monitoring station to a central processing facility (Step 420). The data is then received at the central processing facility and processed by the central processing facility to determine whether the test data is valid (Step 430). Valid test data is then analyzed to generate test results and an appropriate response message to the patient at the remote monitoring station (Step 440). Test results are then stored in the central data repository (Step 450), disseminated along with the appropriate response message (Step 460), and displayed along with other patient information at a remotely located viewing station (Step 470). The lines between the steps of FIG. 4 are shown pointing in both directions to indicate the reciprocal exchange of information between the patient at the remote asthma monitoring station 120 and the physician at the viewing station 180, 200.

The method 400 also includes the step of generating an appropriate request response (not shown) when transmitted test data is determined to be invalid by the central processing facility. This type of response is generated when an operator error or equipment failure has been detected at the remote monitoring station 120 or central processing facility 170.

Figure 5:
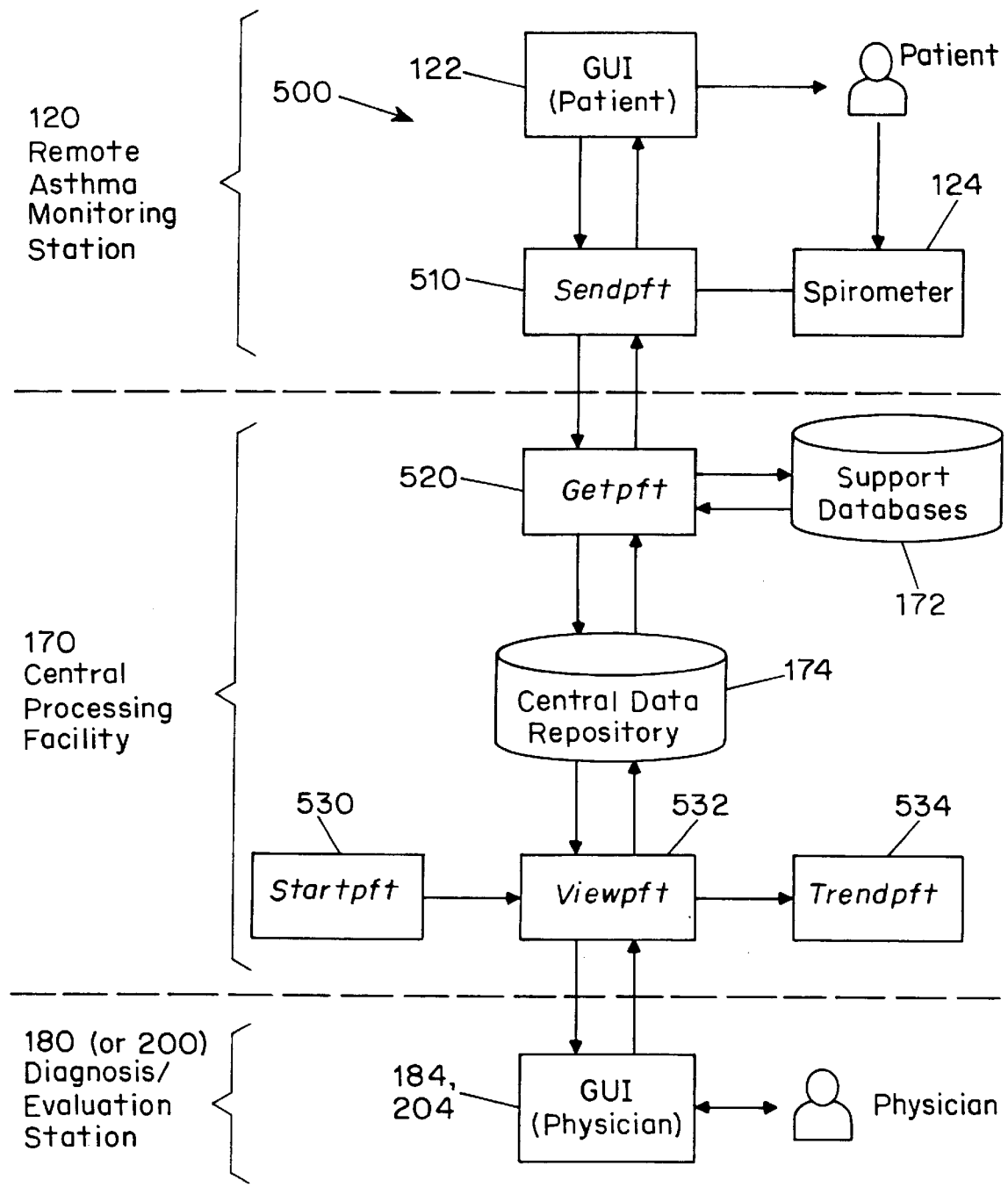
FIG. 5 is a software flow diagram of the program controlling the monitoring system of FIG. 2.

FIG. 5 is a flow diagram for a computer program corresponding to the system of FIG. 2 and for performing the method of FIG. 4. The source code associated with flow diagram of FIG. 5 is contained in the appended microfiche Appendix I, and includes executables "sendpft" 510, "getpft" 520, "startpft" 530, "viewpft" 532 and "trendpft" 534, which are distributed at the remote monitoring asthma station 120, central processing facility 170, and diagnosis/evaluation stations of 180, 200 of FIG. 2, respectively. The computer program also utilizes the symptom diary 128, central data repository 174, support databases 176, 178 and GUI interfaces 122, 184, 204 of FIG. 2. Preferably, the distributed computer program of FIG. 5 is written in C-language and assembler to optimize system performance.

Referring again to FIG. 5, the computer program includes the sendpf executable 510, which is installed in the computing device 126 of the remote monitoring station 120. The senpdf executable 510, together with the symptom diary 128, guides the patient through the self-test procedure and sends the necessary data to the central processing facility 170. Via the patient GUI 122, the patient is asked several questions relating to his' or hers' present respiratory condition. Sendpdf then instructs the patient to perform the self-test using the spirometer 124, which accumulates the required test data until the self-test is completed. When the self-test is completed, the test data is transferred from the spirometer 124 to the computing device 126, preferably via the computing device's serial port, and downloaded along with the responses to the symptom diary questions to the central processing facility 170. Sendpdf downloads the test data and responses (collectively "the data") by selecting an available data link via the wireless/landline modem 130, and by transmitting the data to the central processing facility 170. In case of operator error or equipment failure, the sendpdf executable generates the appropriate error messages for display at the patient GUI 122.

Data transmitted by the remote asthma monitoring station 120 is then received by the central processing facility 170, and processed by the getpft executable 520. The getpft executable 520, along with the startpft, viewpft and trendpft executables 530, 532 and 534, respectively, can be distributed amongst various processors at the central processing facility 170. Preferably, however, each of these executables run on the decision support server 172 of FIG. 2.

Referring again to FIG. 5, the getpft executable receives the data from the remote monitoring station 120 and encodes it using one or more support databases 176 and 178. The support databases, which interface with the getpft executable, may include databases such as MED, ICD-9 and UMLS for reformatting the test date as desired to conform with industry standard data formats. Preferably, the test data is reformatted using an HL7 message format before it is downloaded into the central data repository 174. The getpft executable then retrieves historical data from the central data repository 174 and determines whether an alert condition exists. If an alert condition exists, the getpft executable issues the appropriate alert message to sendpft to notify the patient.

The remaining executables, startpft 530, viewpft 532 and trendpft 534, are used by the physician to evaluate patient data stored in the central data repository 174. The executables can each run on the decision support server 172, or be distributed on different computing platforms as required at the central processing facility 170. Preferably, the executables 530, 532 and 534 are cgi programs that can be invoked by a physician directly from an Internet Web browser. The Web server, again, can be the decision support server 172 or some other computing platform at the central processing facility 170.

In the embodiment of FIG. 5, the startpft executable 530 is used to activate the viewpft and trendpft executables 532 and 534. The startpft executable 530 is activated via a physician GUI 184, 204, preferably a Netscape-compatible Internet Web browser, at the diagnosis/evaluation station 180, 200. Startpft asks the physician to enter information about the data to evaluated, including how the data is to be presented. This data is forwarded to viewpft, which retrieves the requested data from the central data repository 170 and displays it at the diagnosis/evaluation station 180, 200 as requested by the physician. If the physician so desires, the trendpft can be activated to perform statistical trend analysis on the requested data.

The embodiment of FIG. 2 has been tested using ten healthy volunteers and asthma patients. The embodiment utilized the Internet as the communication network 150, the computer program of FIG. 5, and a Netscape-compatible Web browser as the physician GUI 184, 204. Each patient was trained to use the system, and each was equipped with a remote monitoring station 120 for two to 21 days. Each was able to perform FVC tests twice daily, and to upload FVC curves and symptoms scores from their homes to the central data repository 174. The system provided reliable and timely reciprocal exchange of all relevant information between the physician and the remotely located asthma patients.

Based on the system test, the average transmission time from the computing device 126 to the central data repository 174 was shown to be approximately six minutes when using a cellular network for the wireless data link 140, and eight minutes when using a RAM Mobile network. The data transmission rate over these wireless networks did not exceed 9600 bps. When using a 14.4 Kbps landline in place of the wireless path, the average transmission time improved to approximately one minute. In each case, the test results were available for review on a decision support server Web page immediately after transmission.

Although the present invention has been described in connection with particular embodiments thereof, it is to be understood that such embodiments are susceptible of modification and variation without departing from the scope of the inventive concept as defined by the appended claims.

FILE NO. A31572-A - 070050.0864

APPENDIX I:

Source Listings for sendpft, getpft, startpft, viewpft and trendpft

FILE NO. A31572-A - 070050.0864

<u>sendpft</u>

```
#include <stdio.h>      /*ID is defined from file*/  /*04/21/97*/
#include <string.h>     /*28/29*/
#include <stdlib.h>
#include <dos.h>
#include <time.h>
#include <conio.h>
#include <graphics.h>
include <dir.h> pragma inline      //-B use TASM
pragma option -1   //80186 codes
#pragma option -N-  //turn off stack checking
pragma option -G   //speed optimization define ICR_N  1 //interr. control reg.
define IIDR_N 2 //interr. identification d. reg.
#define LCR_N  3 //line control register
#define MCR_N  4 //modem control reg.
#define LSR_N  5 //line status reg.
#define MSR_N  6 //modem status reg.
//#define COM   1 // 1-COM1 2-COM2 3-COM3 4-COM4
//#define Qn 10
#define Ndial 4 // # of attempts to dial
define trLen 30  //120 int COM,mCOM;
int MX[144],MI[144];
float parval[29][3],bestnow[29],bestval[29],valbuf[29][trLen];
char parnam[29][15]={
   "FVC","FEV.5","FEV.5/FVC%","FEV.75","FEV.75/FVC%","FEV1","FEV1/VC%",
   "FEV1/FVC%","FEV1/PEF","FEV3","FEV3/FVC%","PEF","FEF25-75%",
   "FEF25-75/FVC","FEF75-85%","FEF.2-1.2","FEF25%","FEF50%","FEF75%",
   "FMFT","FET","MVVind","FIVC","FIVC/FVC%","PIF","FIF25%","FIF50%",
   "FIF75%","FIF50/FEF50%"};

typedef struct _AUX_MODE_ {
union {
  struct {
```

```
    unsigned char len : 2, //char length
        stop : 1, //#stop-bits
        parity : 2, //parity control
    stuck_parity : 1, //parity fixation
    en_break_ctl : 1, //break
        dlab : 1; //speed divider
    } ctl_word;
  char ctl;
} ctl_aux;

unsigned long baud; // communication speed
} AUX_MODE;

typedef union _MCR_ {
struct {
 unsigned char dtr : 1;
 unsigned char rts : 1;
 unsigned char out1 : 1;
 unsigned char out2 : 1;
 unsigned char diag : 1;
 unsigned char reserv : 3;
 } bit_reg;
 unsigned char byte;
} MCR;

typedef union _MSR_ {
struct {
 unsigned char change_cts : 1;
 unsigned char change_dsr : 1;
 unsigned char change_ri : 1;
 unsigned char change_dcd : 1;
 unsigned char cts : 1;
 unsigned char dsr : 1;
 unsigned char ri : 1;
 unsigned char dcd : 1;
 } bit_reg;
 unsigned char byte;
} MSR;
```

FILE NO. A31572-A - 070050.0864

```
unsigned def_base_adr(int COMN); //define base address
int aux_init(AUX_MODE *mode, int port, int imask); //init COM
//void aux_stat(AUX_MODE *mode, int COMN); //read COM status
//void modem_status(void);
//void prn_status(AUX_MODE *mode, int port); //display status
char aux_inp(int port);   //read byte
void aux_outp(char chr, int port); //send a byte
void dtr_on(int COMN); //set DTR & RTS
void dtr_off(int COMN); //clear DTR & RTS
void aux_inp0(int COMN);   //read byte void aStrOut(char *s);
int Resp(char *message,char *rsp,int waitSec);
void decrypt(char *str);
void noTrans(FILE *datfil);

int Ctrl_Handler(void);
float StoF(char *str);
char *getGRline(char *cp);
int Exp(int row, int nb, unsigned char GR12);
int Ins(int row, int nb, unsigned char GR12);
void NightScore(char *score);
void DayScore(char *score);
//void grDayScore(char *SS);
//void grNightScore(char *SS);
void FVChelp(void);
void doFVC(int ntst);
void drawFVC(void); //(int MX[144], int MI[144]);
void showFVC(void); //(char pn[29][15],float pv[29][3]);
void drawPnt(int x, int y);
void trends(int Nm);
void PtMsg(char *Msg);
void showMsg(char *Msg);
//(char pn[29][15],float pv[29][3],float bv[29][trLen],int Nm);

void main(void)
{
AUX_MODE LCR;

unsigned char a_ch[55][144];
```

FILE NO. A31572-A - 070050.0864

```
unsigned char old,new,mask,shift,b,V12;
char s[10],Fnam[20],Sc[15];
int grX,grY,z,n,x,Npnt,Nrow,top,nbit,nFVC=0,A;
time_t timer,DrTime,tFVCstart,tFVCend,tLastD=1,TrTime=0;
struct tm *tblock;
struct ffblk ffblk;
FILE *f;
int i,j,y,k,l,m,Nmeas=-1;
unsigned char ch;
char s1[512]="",s2[512]="",s3[64]="",s4[64]="",ID[8]="",Phone[20];
//char PhoneN[]=".,,+.23"; //8542477
char PhoneN[4][8]={"8543197","8549924","8542477","8543726"};
char IP[]="')0'/4*.4/.223"; //128.59.160.100
char LogInID[]="^fe^jap"; //homepft
char Pass[]="blf`n`oq"; //lungtest
unsigned char p[26000];
char *c=p,*c1,*c2,msg[512],PrePost,mINIT[128];
char msgIn[400]="",msgOut[400]="{**}";

ctrlbrk(Ctrl_Handler);
f=fopen("homepft.id","rt");
fscanf(f,"%s%d%d%s%s",ID,&COM,&mCOM,Phone,mINIT);
fclose(f); //printf("%s %d %d %s\n",ID,COM,mCOM,Phone); exit(0);

decrypt(IP); decrypt(LogInID); decrypt(Pass); //decrypt(PhoneN);
for (i=0;i<29;i++) bestval[i]=0;

StartOver:

/*zoom HP text mode*/
asm { MOV AH,0
      MOV AL,0x84
      INT 0x10 } clrscr();
 // 12345678912345678901234567890123457890
puts("\n");
puts(" COLUMBIA-PRESBYTERIAN MEDICAL CENTER\n");
puts(" Welcome to Asthma Monitoring Program.\n");
puts(" This program allows to monitor asthma");
```

FILE NO. A31572-A - 070050.0864

```
puts(" severity at home using symptom diary");
puts(" and pulmonary function test.");
puts(" The results of self-testing are sent");
puts(" to CPMC and immediately become");
puts(" available for review by a doctor.\n");
puts("     To start symptom diary please");
puts("        PUSH ANY BUTTON.");
ch=getch();

timer = time(NULL); tblock = localtime(&timer);
if (difftime(timer,tLastD)>14400.0) {
  if ((tblock->tm_hour>4)&&(tblock->tm_hour<16)) NightScore(Sc);
  else {DayScore(Sc); PtMsg(msgOut);}
  tLastD=timer; DrTime=(time_t)difftime(time(NULL),timer);
} do {
 clrscr();
 puts("\n\n\nWHEN DID YOU USE YOUR BRONCHODILATOR\n(RELIEVER) LAST TIME?");
 puts("");
 puts(" 0 - LESS THAN 30 MINUTES AGO");
 puts(" 1 - 30 MINUTES TO TWO HOURS AGO");
 puts(" 2 - TWO TO FOUR HOURS AGO");
 puts(" 3 - MORE THAN FOUR HOURS AGO");
 puts("");
 printf("ENTER YOUR CHOICE: "); scanf("%1s",s1);
}
while ((*s1<48)||(*s1>51));
PrePost=*s1;

strcpy(s2,"\n\n THE SYMPTOM DIARY HAS BEEN COMPLETED.\n\n\n");
tFVCstart=time(NULL);

for (i=0;i<29;i++) bestnow[i]=0;

startFVC:
c=p;
do {
 clrscr(); puts(s2);
```

- 31 -

FILE NO. A31572-A - 070050.0864

```
// 12345678901234567890123456789012345678901234567890
    puts("Please be ready for the");
    printf("    SPIROMETRY test #%d.\n",nFVC+1);
    puts("To obtain reliable data you should");
    printf("repeat the test three times.\n\n");
    puts(" 1 - READY FOR THE TEST");
    puts(" 2 - NEED HELP");
    puts(" 3 - REFUSE TO DO\n");
    printf("Please enter your choice: "); scanf("%1s",s1); *s2=0;
    if (*s1=='#') exit(0);
}
while ((*s1<49)||(*s1>51));

if (*s1==50) {FVChelp(); goto startFVC;}
if (*s1==51) if (nFVC>0) goto sendData;
else {strcpy(s2,"\n\nYou have to do spirometry\nat least one time!\n\n");
    goto startFVC;} doFVC(nFVC);

aux_inp0(COM); //clean the input
LCR.ctl_aux.ctl_word.len=3;/*8bits*/ LCR.ctl_aux.ctl_word.stop=0;/*1bit*/
LCR.ctl_aux.ctl_word.parity=0;    LCR.ctl_aux.ctl_word.stuck_parity=0;
LCR.ctl_aux.ctl_word.en_break_ctl=0; LCR.ctl_aux.ctl_word.dlab=0;
LCR.baud=9600;
aux_init(&LCR, COM, 0); dtr_on(COM); dtr_on(mCOM);
        /*COM1-0x3F8 COM3-0x3E8*/
asm {
    XOR  AH,AH
    XOR  BL,BL
    MOV  BH,0xE
    MOV  CL,76
    MOV  CH,87
    PUSH SI
    MOV  SI,c
    PUSH DI
    PUSH BP
    MOV  BP,7691
    CLI }
COMIN:
```

FILE NO. A31572-A - 070050.0864

```
asm { MOV DX,0x3FD
    IN   AL,DX
    TEST AL,00000001B
    JZ   COMIN
    MOV  DX,0x3F8
    IN   AL,DX
    MOV  BYTE PTR[SI],AL
    CMP  AL,0x4B
    JNE  NOTESC
    CMP  AH,0x1B
    JNE  NOTESC
    TEST BL,BL
    JNZ  GRNEXT
    MOV  DI,SI
    ADD  DI,BP
    INC  BL
    JMP  NOTESC }
GRNEXT:
asm { INC BL
    CMP  BL,CL
    JBE  NOTESC
    CMP  BYTE PTR[DI],BH
    JNE  COMSTOP
    CMP  BL,CH
    JA   COMSTOP }
NOTESC:
asm { MOV AH,AL
    INC  SI
    JMP  COMIN }
COMSTOP:
asm { MOV CX,283 }
GOLOOP:
asm { MOV DX,0x3FD
    IN   AL,DX
    TEST AL,00000001B
    JZ   GOLOOP
    MOV  DX,0x3F8
    IN   AL,DX
    LOOP GOLOOP
    STI
```

FILE NO. A31572-A - 070050.0864

```
        MOV  AL,BYTE PTR[DI]
        POP  BP
        POP  DI
        POP  SI
        MOV  s,AL
   }
//for (x=i;x<=i+283;x++) p[x]=aux_inp(COM); Npnt=x-1;

if (s[0]!=0xE) {Nrow=45; V12=1;} else {Nrow=54; V12=0;} tFVCend=time(NULL);    //the timer was switched off!
//printf("%ld %ld %d\n",tFVCstart,tFVCend,(int)difftime(tFVCend,tFVCstart));

/*
z=i=old=x=0; //n=30000;
do {
 ch=p[i++]=aux_inp(COM);
 if ((old==0x1B)&&(ch==0x4B)) {
    if (x==0) z=i; x++;
    if (x>76) if (p[z+7690]!=0xE) break; else if (x>87) break;
 }
 old=ch;
}
while (1);
Npnt=i-1; if (p[z+7690]!=0xE) {Nrow=45; V12=1;} else {Nrow=54; V12=0;}
    Npnt=25000;
f=fopen("va.dmp","wb"); for (i=0;i<=Npnt;i++) {ch=p[i]; fputc(ch,f);}
fclose(f);

f=fopen("v.dmp","rb"); i=0;   Nrow=54; V12=0;
while (feof(f)==0) {ch=fgetc(f); p[i++]=ch; }
fclose(f);     */

//f=fopen("sendpft.dat","wt");
timer = time(NULL); tblock = localtime(&timer);
sprintf(Fnam,"%c%1d%02d%02d%02d.dr",
tblock->tm_mon+65,nFVC,tblock->tm_mday,tblock->tm_hour,tblock->tm_min);
f=fopen(Fnam,"w"); /*fprintf(f,"%s\n",s1); fclose(f);*/ fprintf(f,"HomePFT_ID: %s\n",ID);
```

- 34 -

FILE NO. A31572-A - 070050.0864

```
c=strstr(c,"Date"); sscanf(c,"%s%s",s1,s2);
c=strstr(c,"Time"); sscanf(c,"%s%s",s3,s4);
for (i=0;i<2;i++) {c1=strchr(s2,'/'); *c1++=' ';c2=strchr(s4,':'); *c2++=' ';}
sscanf(s2,"%d%d%d",&i,&j,&y); sscanf(s4,"%d%d%d",&k,&l,&m);
fprintf(f,"%d %d %d %d %d %d\n",y,i,j,k,l,m);

c=strstr(c,"Age");    sscanf(c,"%s%s",s3,s4); fprintf(f,"%s ",s4);
c=strstr(c,"Height"); sscanf(c,"%s%s",s3,s4); fprintf(f,"%s ",s4);
c=strstr(c,"Sex");    sscanf(c,"%s%s",s3,s4); fprintf(f,"%s ",s4);
c=strstr(c,"Origin"); sscanf(c,"%s%s",s3,s4); fprintf(f,"%s ",s4);
fprintf(f,"%c %d %d",PrePost,(int)DrTime,(int)difftime(tFVCend,tFVCstart));
fprintf(f,"*%d\n",nFVC+1);         /* x x x in some ver*/

/*variability*/
c=strstr(c,parnam[0]); i=0;
do s1[i++]=*c++; while (*c!='\n'); s1[i]='\0'; fprintf(f,"%s\n",s1);

c=strstr(c,"test"); sscanf(c,"%s%s",s1,s2); fprintf(f,"%s\n",s2);

for (i=0;i<2;i++) {c=strchr(c,'\n'); c++;}
i=0; do s1[i++]=*c++; while (*c!='\n'); s1[i]='\0'; fprintf(f,"%s\n",s1);

for (i=0;i<29;i++) {
  c=strstr(c,parnam[i]); sscanf(c,"%s%s%s%s",s1,s2,s3,s4);
  parval[i][0]=StoF(s2); parval[i][1]=StoF(s3); parval[i][2]=StoF(s4);
  fprintf(f,"%s %s %s\n",s2,s3,s4);} c=strstr(c,"Results"); c=strchr(c,0x30); c++; i=0;
do s1[i++]=*c++; while (*c!='\n'); s1[i]='\0';
fprintf(f,"%s\n",s1);

/*graph*/
n=0; new=0; i=0; grY=0; old=0;
for (x=0;x<144;x++) {MX[x]=0; MI[x]=0; for (i=0;i<55;i++) a_ch[i][x]=0;}
for (i=0;i<31;i++) c=getGRline(c);
for (i=0;i<Nrow;i++)
  {c=getGRline(c); c+=27; for (x=0;x<144;x++) ch=a_ch[i][x]=*c++;} if (V12) top=22; else top=26;
```

FILE NO. A31572-A - 070050.0864

```
for (x=135;x>1;x--)    //do 0,1 after 143-8
    for (i=top;i>=0;i--) if (a_ch[i][x]!=0) {  //do 23 after
        if (i==26) {
          if ((a_ch[i][x]&0xFC)==0) continue;
             shift=4; n=3;
          while ((a_ch[i][x]&shift)==0) {shift<<=1; n++;} }
        else {
          shift=1; n=1;
          while ((a_ch[i][x]&shift)==0) {shift<<=1; n++;} } /*
          shift=0x80; n=8;
          while ((a_ch[i][x]&shift)==0) {shift>>=1; n--;}    */
        MX[x]=Exp(i,n,V12); break;
    }

//vertical search for x=0,1
if (V12) {grY=180; top=22;} else {grY=210; top=26;}
for (x=1;x>=0;x--) {
    if (V12&&((a_ch[23][x]&0x40)!=0)) MX[x]=1;
    else
    if (V12&&((a_ch[23][x]&0x80)!=0)) MX[x]=2;
    else {
        for (i=top;i>=0;i--) if (a_ch[i][x]!=0)
        {
        shift=1; n=1;
        while ((a_ch[i][x]&shift)==0) {shift<<=1; n++;}
        MX[x]=Exp(i,n,V12);
        if (MX[x]%15==0) {
         if (n<8) {       //check whether another bit is set
         do {shift<<=1; n++;} while ((n<9)&&((a_ch[i][x]&shift)==0));
         if (n<9) MX[x]=Ins(i,n,V12); else MX[x]=0; }//if n<8
         else MX[x]=0;
        }//if MX%15
        if (MX[x]>0) break;
        }//for22-0
        if (MX[x]==0) {
          y=32000; for (z=0;z<=grY;z=z+15)
          if (abs(z-MX[x+1])<y) {y=abs(z-MX[x+1]); MX[x]=z;}; }
    }//else
}//for1-0
```

FILE NO. A31572-A - 070050.0864

```
//horiz search for y=1,2
if (V12) {top=23; mask=0x80; b=0x40;} else {top=26; mask=2; b=1;}
for (x=143;x>=0;x--) if (MX[x]>0) break; x++;
while (x<=135) {
if (x%24==0) {
y=x+1;
if ((a_ch[top][y]&mask)!=0) MX[y]=2; else if ((a_ch[23][y]&b)!=0) MX[y]=1;
if (MX[y]>0) {MX[x]=(MX[x-1]+MX[y])/2; x=y++;} else break; }
else {
if ((a_ch[23][x]&mask)!=0) MX[x++]=2;
else if ((a_ch[23][x]&b)!=0) MX[x++]=1;
else break;}
}//while /* FIV */
if (V12) {top=23; b=0xF; mask=8;  nbit=4;}
   else {top=27; b=0x3F; mask=0x20; nbit=6;}
for (x=143;x>1;x--) {   //do 0,1 after
    for (i=Nrow;i>top;i--)   //do 23-24 after
       if (a_ch[i][x]!=0) {
          if (i==top+1) {
          if ((a_ch[i][x]&b)==0) break;
          shift=mask; n=nbit;
          while ((a_ch[i][x]&shift)==0) {shift>>=1; n--;} }
          else {
          shift=1; n=1;
          while ((a_ch[i][x]&shift)==0) {shift<<=1; n++;} }
          MI[x]=Ins(i,n,V12);
          break;
       } //if
} //for 143

//vert. search x=0,1
if (V12) {top=23; b=0x1F; mask=0x10; nbit=5; grY=180;}
    else {top=27; b=0x7F; mask=0x40; nbit=7; grY=210;}
for (x=1;x>=0;x--) {
  for (i=top;i<=Nrow;i++) {
    if (a_ch[i][x]!=0)
      if (i==top) {
        if ((a_ch[i][x]&b)==0) continue;
```

- 37 -

FILE NO. A31572-A - 070050.0864

```
    shift=mask; n=nbit;
    while ((a_ch[i][x]&shift)==0) {shift>>=1; n--;} }
  else {
    shift=1; n=1;
    while ((a_ch[i][x]&shift)==0) {shift<<=1; n++;} }
  MI[x]=Ins(i,n,V12);
  if ((MI[x]%15)!=0) {
      if (n<8) {
      do {shift<<=1; n++;} while ((n<9)&&((a_ch[i][x]&shift)==0));
      if (n<9) MI[x]=Ins(i,n,V12); else MI[x]=0; }//if n<8
      else MI[x]=0;
      }//if MX%15
  }
  if ((MI[x]==0)&&(MI[x+1]>0)) {
    y=32000;
    for (z=0; z<=grY; z+=15)
      {if (abs(z-MI[x+1])<y) y=abs(z-MI[x+1]); MI[x]=z;}
  }
if (MI[x]>MI[x+1]) {MI[x]=0; break;}
} for (i=0;i<144;i++) fprintf(f,"%c",(unsigned char)(MX[i]+35));
fprintf(f,"\n");

for (i=0;i<144;i++) fprintf(f,"%c",(unsigned char)(MI[i]+35));
fprintf(f,"%s\n",Sc);

fprintf(f,"%s\n",msgOut); strcpy(msgOut,"{**}");
fclose(f);

for (i=0;i<29;i++) if (bestnow[i]<parval[i][1]) bestnow[i]=parval[i][1];
printf("\7"); *s2=0; if (++nFVC<3) goto startFVC;

//printf("%s\n",Fnam); exit(0);
/*transmit the data*/ sendData:

nFVC=0; Nmeas++; x=Nmeas%trLen;
for (i=0;i<29;i++) {
```

- 38 -

FILE NO. A31572-A - 070050.0864

```
    if (bestval[i]<bestnow[i]) bestval[i]=bestnow[i];
    valbuf[i][x]=bestnow[i];
}
//goto fDia;

clrscr(); A=144+1; TrTime=time(NULL);
//prn_status(&LCR, mCOM);
LCR.ctl_aux.ctl_word.len=3;/*8bits*/ LCR.ctl_aux.ctl_word.stop=0;/*1bit*/
LCR.ctl_aux.ctl_word.parity=0;    LCR.ctl_aux.ctl_word.stuck_parity=0;
LCR.ctl_aux.ctl_word.en_break_ctl=0; LCR.ctl_aux.ctl_word.dlab=0;
LCR.baud=2400; //9600
aux_init(&LCR, mCOM, 0);
//prn_status(&LCR,mCOM);   modem_status();
//dtr_on(mCOM); //modem_status(); printf("\n");

printf("Checking the modem ... ");
//strcpy(p,"AT&Fq0v1e1\r"); strcpy(msg,"OK\r\n");
//strcpy(p,"AT&Fq0v1e1s0=0&C1&D2&Q5&K3&S1W2S95=18&W\r"); V.42bis
//strcpy(p,"AT&Fq0v1e1s0=0&C1&D2&Q5&K3&S1S46=136S48=128W2S95=18&W\r
"); MNP4
sprintf(p,"AT%s\r",mINIT); strcpy(msg,"OK\r\n");
if (Resp(p,msg,60)) puts("OK"); else {noTrans(f); goto StartOver;}
/*else {                    /*f is already closed!*/
    delay(2500); aStrOut("+++"); delay(2500); Resp("ATH\r",msg,30);
    if (Resp(p,msg,30)) puts("OK"); else {noTrans(f); goto StartOver;}
} */

//    12345678901234567890123456789012345678 90
for (i=0;i<Ndial;i++) {
printf("Connecting to the remote server ... ");
strcpy(p,"ATD");
strcat(p,Phone); strcat(p,PhoneN[i]); strcat(p,"\r"); strcpy(msg,">");
if (Resp(p,msg,120)) {puts("OK"); break;}
if (strstr(p,"NO DIALTONE")!=NULL)
    {puts("\n            NO DIALTONE"); noTrans(f); goto StartOver;}
if (strstr(p,"BUSY")!=NULL) puts("BUSY");
if (i==Ndial-1) {noTrans(f); goto StartOver;}
delay(1000);
}
```

FILE NO. A31572-A - 070050.0864

```
printf("Loging in ... ");
strcpy(p,"cucis\r"); strcpy(msg,"login: ");
if (Resp(p,msg,120)) puts("OK"); else {noTrans(f); goto StartOver;} printf("Checking the password ... ");
strcpy(p,LogInID); strcat(p,"\r"); strcpy(msg,"Password: ");
if (Resp(p,msg,60)==0) {noTrans(f); goto StartOver;};

strcpy(p,Pass); strcat(p,"\r"); strcpy(msg,">");
if (Resp(p,msg,60)) puts("OK"); else {noTrans(f); goto StartOver;} while (!findfirst("*.dr",&ffblk,0)) {
printf("Sending the data ... ");
aStrOut("@\r"); aStrOut("telnet telnet telnet\n");

f=fopen(ffblk.ff_name,"r"); //f=fopen(Fnam,"r"); f=fopen("sendpft.dat","r");
for (i=0; i<38; i++) {
   fgets(p,512,f);
   if (i<36) aStrOut(p);
   if (i==36)
     for (j=0;j<144;j++) {sprintf(msg,"%d\n",p[j]); aStrOut(msg);}
   if (i==37) {
     for (j=0;j<144;j++) {sprintf(msg,"%d\n",p[j]); aStrOut(msg);}
     ch=p[144]; sprintf(msg,"%c\n",ch); aStrOut(msg);
     if (ch=='E') z=10; else if (ch=='M') z=3; else z=0;
     if (z>0)
       for (j=A;j<A+z;j++) {sprintf(msg,"%d\n",p[j]); aStrOut(msg);}
   }
} while (fgets(p,512,f)!=NULL) aStrOut(p);
fclose(f);

strcpy(p,"!END\n"); strcpy(msg,">");
if (Resp(p,msg,60)) puts("OK"); else {noTrans(f); goto StartOver;}
c1=strstr(p,"!MSG"); while(*c1++!='\n'); c2=strstr(c1,"!MSG");
c=s1; while (c1<c2) *c++=*c1++; *c='\0'; puts(s1); strcpy(msgIn,s1);
remove(ffblk.ff_name);
}
```

FILE NO. A31572-A - 070050.0864

```
printf("Closing the connection ... ");
strcpy(p,"exit\r"); strcpy(msg,">");
if (Resp(p,msg,60)) puts("OK"); else {noTrans(f); goto StartOver;} printf("Hanging up ... ");
strcpy(p,"q\r"); strcpy(msg,"NO CARRIER");
if (Resp(p,msg,60)) puts("OK"); else {noTrans(f); goto StartOver;}

//strcpy(p,"ATH\r"); strcpy(msg,"OK\r\n"); Resp(p,msg,60); printf("%s\n",p);
dtr_off(mCOM); dtr_off(COM); TrTime=(time_t)difftime(time(NULL),TrTime);

fDia:
//remove(Fnam);
clrscr(); printf("%c",7);
puts(" YOU GOT A MESSAGE FROM THE CPMC SERVER:");
puts(s1);
puts("_____");
puts("");
puts("        CONGRATULATIONS!");
puts(" You have successfully completed");
puts(" self-testing procedures.\n");
do {
    puts("\n");
    puts(" 0 - START OVER");
    puts(" 1 - SHOW THE LATEST RESULTS");
    puts(" 2 - SHOW TRENDS");
    puts(" 3 - SHOW THE LAST MESSAGE\n");
    printf("ENTER YOUR CHOICE: "); scanf("%1s",s1);
    if (*s1==48) break;
    if (*s1==49) {showFVC();drawFVC();}
    if (*s1==50) trends(Nmeas);
    if (*s1==51) showMsg(msgIn);
    clrscr(); puts("\n\n\n\n\n");
}
while (1);
/*
puts(" To start over please push any button.");
//   123456789012345678901234567890
timer=time(NULL)+120;
while (timer>time(NULL)) if (kbhit()) {ch=getch(); break;}
```

FILE NO. A31572-A - 070050.0864

```
*/
goto StartOver;

} int Ctrl_Handler(void)
{
} void noTrans(FILE *datfil)
{
char ch;
time_t timer;
fclose(datfil);
//clrscr();
puts("\n\n");
puts("    Transmission was not completed.");
puts("      Please check your modem.");
puts("     The data was stored locally.\n");
puts("  To start over please push any button.");
//    123456789012345678901234567890123456789 0
timer=time(NULL)+120;
while (timer>time(NULL)) if (kbhit()) {ch=getch(); break;}
} float StoF(char *str) {
if (str[0]=='-') {strcpy(str,"0"); return(0.0);}
else return((float)atof(str));
} char *getGRline(char *cp) {
do if ((*cp==0x1B)&&(*(cp+1)==0x4B)) break; else cp++; while (1);
return(cp+2);
}
/*
void modem_status(void)
{
unsigned char data;
unsigned int base_adr;
```

- 42 -

FILE NO. A31572-A - 070050.0864

```c
base_adr=def_base_adr(COM);
printf("\nMSR_N = %x",data=(unsigned char) inp(base_adr+MSR_N));
printf(" MCR_N = %x",data=(unsigned char) inp(base_adr+MCR_N));
} */ void dtr_on(int COMN)
{
unsigned char MCR; //modem control reg.
unsigned int base_adr;
base_adr=def_base_adr(COMN); MCR=inp(base_adr+MCR_N); MCR|=3;//3
outp(base_adr+MCR_N,MCR);
} int aux_init(AUX_MODE *mode, int COMN, int imask)
{                   //imask=0 if interr. are cancelled
unsigned div, base_adr;
char ctl;
base_adr=def_base_adr(COMN);
ctl=inp(base_adr+LSR_N); //read LSR to erase error bits
switch (mode->baud) {
    case    110  : div=1040; break;
    case    150  : div=768;  break;
    case    300  : div=384;  break;
    case    600  : div=192;  break;
    case    1200 : div=96;   break;
    case    2400 : div=48;   break;
    case    4800 : div=24;   break;
    case    9600 : div=12;   break;
    case    19200 : div=6;   break;
    case    38400 : div=3;   break;
    case    57600 : div=2;   break;
    case    115200: div=1;   break;
    default:    return(-1);
};         //write speed divider
ctl=inp(base_adr+LCR_N); outp(base_adr+LCR_N,ctl|0x80);
outp(base_adr+ICR_N, (div>>8)&0x00FF);  outp(base_adr, div&0x00FF);
outp(base_adr+LCR_N, mode->ctl_aux.ctl&0x7F); //write new control byte
outp(base_adr+ICR_N,imask);
return(0);
```

FILE NO. A31572-A - 070050.0864

```c
} void dtr_off(int COMN)
{
unsigned char MCR; //modem control reg.
unsigned int base_adr;
base_adr=def_base_adr(COMN); MCR=inp(base_adr+MCR_N); MCR&=0xFC;
outp(base_adr+MCR_N,MCR);
}

/*
void aux_stat(AUX_MODE *mode, int COMN) //read COM status
{
unsigned long b;
unsigned int base_adr;
base_adr=def_base_adr(COMN);
mode->ctl_aux.ctl=(char)inp(base_adr+LCR_N); //read LCR
outp(base_adr+LCR_N,mode->ctl_aux.ctl | 0x80); //enable speed data
b=inp(base_adr+ICR_N); b<<=8; b+=inp(base_adr); //read speed divider
switch (b) {
    case 1040: b=110;    break;
    case  768: b=150;    break;
    case  384: b=300;    break;
    case  192: b=600;    break;
    case   96: b=1200;   break;
    case   48: b=2400;   break;
    case   24: b=4800;   break;
    case   12: b=9600;   break;
    case    6: b=19200;  break;
    case    3: b=38400;  break;
    case    2: b=57600;  break;
    case    1: b=115200; break;
    default:   b=0;      break;
};
mode->baud=b;
outp(base_adr+LCR_N,mode->ctl_aux.ctl & 0x7F); //restore LCR
}
*/
```

FILE NO. A31572-A - 070050.0864

```
char aux_inp(int COMN)   //read byte
{                  unsigned i;
int x,y;
unsigned status_reg, base_adr;
base_adr=def_base_adr(COMN); status_reg=base_adr+LSR_N;
while((inp(status_reg)&1)==0);
return(inp(base_adr));
} void aux_outp(char chr, int COMN) //send byte
{
unsigned status_reg, base_adr;
base_adr=def_base_adr(COMN); status_reg=base_adr+LSR_N;
while((inp(status_reg)&0x20)==0); outp(base_adr,chr);
} unsigned def_base_adr(int COMN)
{   //return( *((unsigned far *) MK_FP(0x40,(COMN-1)*2)) );
switch (COMN) {
    case 1:  return(0x3F8);
    case 2:  return(0x2F8);
    case 3:  return(0x3E8);
    case 4:  return(0x2E8);
    default: return(0x3F8);
};
} int Exp(int row, int nb, unsigned char GR12)
{
if (GR12) return((nb+2)+(23-row-1)*8); else return(8*(26-row)+nb);
} int Ins(int row, int nb, unsigned char GR12)
{
if (GR12) return((9-nb)+5+(row-24)*8); else return(8*(row-27)+(8-nb));
}
```

FILE NO. A31572-A - 070050.0864

```c
void aux_inp0(int COMN)   //read byte
{
unsigned status_reg, base_adr, rs;
base_adr=def_base_adr(COMN); status_reg=base_adr+LSR_N;
while (inp(status_reg)&1) rs=inp(base_adr);
} void NightScore(char *scr)
{
char sc1[4],R[8];
int r;
*scr++='M';
while (kbhit()) getch();
do {
 clrscr();
 puts("\nGOOD MORNING!\n");
 puts("PLEASE ESTIMATE THE DISTURBANCE");
 puts("OF YOUR SLEEP BY ASTHMA:");
 puts("");
 puts(" 0 - NONE");
 puts(" 1 - MILD");
 puts(" 2 - MODERATE");
 puts(" 3 - SEVERE");
 puts("");
 printf("ENTER YOUR SCORE: "); scanf("%1s",sc1);
}
while ((*sc1<48)||(*sc1>51));
*scr++=*sc1+35;

do {
 clrscr();
 puts("\n\n\n\n\nPLEASE ENTER");
 printf("NUMBER OF AWAKENING BY ASTHMA: "); scanf("%3s",R);
 r=atoi(R); if ((r==0)&&(R[1]!='\0')) continue;
 if ((r==0)&&(R[0]!='0')) continue; if (r<99) break; }
while (1);
*scr++=r+35;

do {
 clrscr();
```

- 46 -

FILE NO. A31572-A - 070050.0864

```
    puts("\n\n\n\n\n       NIGHTTIME RELIEVER USE\n\n\n");
    printf("PLEASE ENTER NUMBER OF PUFFS OF\nBRONCHODILATOR DURING THE NIGHT: ");
    scanf("%3s",R); r=atoi(R); if ((r==0)&&(R[1]!='\0')) continue;
    if ((r==0)&&(R[0]!='0')) continue; if (r<99) break; }
 while (1);
 *scr++=r+35;

*scr=0;
 } void DayScore(char *scr)
 {
 int r;
 char sc1[4],R[8];
 *scr++='E';
 while (kbhit()) getch();
 do {
  clrscr();
  puts("\nHELLO! PLEASE DESCRIBE THE ASTHMA");
  puts("SYMPTOMS YOU EXPERIENCED TODAY:");
  puts("\n");
  puts("WHEEZE");
  puts("");
  puts(" 0 - NONE");
  puts(" 1 - MILD");
  puts(" 2 - MODERATE");
  puts(" 3 - SEVERE");
  puts("");
  printf("ENTER YOUR SCORE: "); scanf("%1s",sc1);
  }
  while ((*sc1<48)||(*sc1>51));
  *scr++=*sc1+35;

do {
  clrscr();
  puts("\n");
  puts("COUGH");
  puts("");
  puts(" 0 - NONE");
```

FILE NO. A31572-A - 070050.0864

```
   puts(" 1 - MILD");
   puts(" 2 - MODERATE");
   puts(" 3 - SEVERE");
   puts("");
   printf("ENTER YOUR SCORE: "); scanf("%1s",sc1);
   }
   while ((( *sc1<48)||(*sc1>51));
   *scr++=*sc1+35;

do {
    clrscr();
    puts("\n");
    puts("SPUTUM PRODUCTION");
    puts("");
    puts(" 0 - NONE");
    puts(" 1 - MILD");
    puts(" 2 - MODERATE");
    puts(" 3 - SEVERE");
    puts("");
    printf("ENTER YOUR SCORE: "); scanf("%1s",sc1);
   }
   while ((( *sc1<48)||(*sc1>51));
   *scr++=*sc1+35;

do {
    clrscr();
    puts("\n");
    puts("CHEST TIGHTNESS");
    puts("");
    puts(" 0 - NONE");
    puts(" 1 - MILD");
    puts(" 2 - MODERATE");
    puts(" 3 - SEVERE");
    puts("");
    printf("ENTER YOUR SCORE: "); scanf("%1s",sc1);
   }
   while ((( *sc1<48)||(*sc1>51));
   *scr++=*sc1+35;

do {
```

FILE NO. A31572-A - 070050.0864

```
    clrscr();
    puts("\n");
    puts("SHORTNESS OF BREATH");
    puts("");
    puts(" 0 - NONE");
    puts(" 1 - MILD");
    puts(" 2 - MODERATE");
    puts(" 3 - SEVERE");
    puts("");
    printf("ENTER YOUR SCORE: "); scanf("%1s",sc1);
  }
  while ((*sc1<48)||(*sc1>51));
  *scr++=*sc1+35;

do {
    clrscr();
    puts("\n");
    puts("LIMITATION OF PHYSICAL ACTIVITY");
    puts("");
    puts(" 0 - NONE");
    puts(" 1 - MILD");
    puts(" 2 - MODERATE");
    puts(" 3 - SEVERE");
    puts("");
    printf("ENTER YOUR SCORE: "); scanf("%1s",sc1);
  }
  while ((*sc1<48)||(*sc1>51));
  *scr++=*sc1+35;

do {
    clrscr();
    puts("\n");
    puts("OVER-ALL USE OF ASTHMA MEDICATIONS");
    puts("");
    puts(" 0 - AS USUAL");
    puts(" 1 - SLIGHTLY INCREASED");
    puts(" 2 - SIGNIFICANTLY INCREASED");
    puts(" 3 - MAXIMAL");
    puts("");
    printf("ENTER YOUR SCORE: "); scanf("%1s",sc1);
```

FILE NO. A31572-A - 070050.0864

```
}
while ((*sc1<48)||(*sc1>51));
*scr++=*sc1+35;

do {
 clrscr();
 puts("\n");
 puts("EXPOSURE TO ASTHMA TRIGGERS");
 puts("");
 puts(" 0 - NONE");
 puts(" 1 - MILD");
 puts(" 2 - MODERATE");
 puts(" 3 - SEVERE");
 puts("");
 printf("ENTER YOUR SCORE: "); scanf("%1s",sc1);
}
while ((*sc1<48)||(*sc1>51));
*scr++=*sc1+35;

do {
 clrscr();
 puts("\n");
 puts("OVER-ALL ESTIMATE OF ASTHMA");
 puts("");
 puts(" 0 - NONE");
 puts(" 1 - MILD");
 puts(" 2 - MODERATE");
 puts(" 3 - SEVERE");
 puts("");
 printf("ENTER YOUR SCORE: "); scanf("%1s",sc1);
}
while ((*sc1<48)||(*sc1>51));
*scr++=*sc1+35;

do {
 clrscr();
 puts("\n\n\n\n    DAYTIME RELIEVER USE");
 printf("\n\n\nPLEASE ENTER THE NUMBER OF PUFFS \nOF BRONCHODILATOR DURING THE DAY: ");
 //scanf("%3s",R);
```

FILE NO. A31572-A - 070050.0864

```
gets(R); r=atoi(R); if ((r==0)&&(R[1]!='\0')) continue;
if ((r==0)&&(R[0]!='0')) continue; if (r<99) break; }
while (1);
*scr++=r+35;

*scr=0;
}

/*********
void DayScore(char *scr)
{
char sc1,sc2;
sc1=sc2=0;
do {
 clrscr();
 puts("HELLO! PLEASE DESCRIBE THE ASTHMA");
 puts("SYMPTOMS YOU EXPERIENCED TODAY:");
 sputs("");
 puts("WHEEZE");
 puts("");
 puts("0 - NONE");
 puts("1 - LITTLE");
 puts("2 - MODERATELY BAD");
 puts("3 - SEVERE");
 puts("");
 if (sc1==0) {
  puts("ENTER YOUR SCORE: "); sc1=getch(); if ((sc1<48)||(sc1>51)) sc1=0; }
 else {
  printf("YOU HAVE ENTERED %c.\n",sc1);
  puts ("TO CONFIRM YOUR CHOICE");
  printf("PLEASE ENTER %c AGAIN:",sc1);
  sc2=getch(); if (sc1!=sc2) sc1=sc2=0; }
}
while (sc2==0);
*scr++=sc1;

sc1=sc2=0;
do {
 clrscr();
```

FILE NO. A31572-A - 070050.0864

```
puts("");
puts("COUGH");
puts("");
puts("0 - NONE");
puts("1 - OCCASIONAL");
puts("2 - FREQUENT");
puts("");
if (sc1==0) {
 puts("ENTER YOUR SCORE: "); sc1=getch(); if ((sc1<48)||(sc1>50)) sc1=0; }
else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
do {
 clrscr();
 puts("");
 puts("SPUTUM");
 puts("");
 puts("0 - NONE");
 puts("1 - OCCASIONAL BLOTS (LESS THAN 3 TSPS)");
 puts("2 - A LOT (MORE THAN 3 TSPS)");
 puts("");
if (sc1==0) {
 puts("ENTER YOUR SCORE: "); sc1=getch(); if ((sc1<48)||(sc1>50)) sc1=0; }
else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
```

FILE NO. A31572-A - 070050.0864

```
do {
 clrscr();
 puts("");
 puts("CHEST TIGHTNESS");
 puts("");
 puts("0 - NONE");
 puts("1 - MILD");
 puts("2 - MARKED");
 puts("");
 if (sc1==0) {
  puts("ENTER YOUR SCORE: "); sc1=getch(); if ((sc1<48)||(sc1>50)) sc1=0; }
 else {
  printf("YOU HAVE ENTERED %c.\n",sc1);
  puts ("TO CONFIRM YOUR CHOICE");
  printf("PLEASE ENTER %c AGAIN:",sc1);
  sc2=getch(); if (sc1!=sc2) sc1=sc2=0; }
}
while (sc2==0);
*scr++=sc1;

sc1=sc2=0;
do {
 clrscr();
 puts("");
 puts("SHORTNESS OF BREATH");
 puts("");
 puts("0 - NONE");
 puts("1 - MILD (CHOKING SENSATION WITH SOME");
 puts("    CHEST TIGHTNESS, ABLE TO MOVE ABOUT)");
 puts("2 - MODERATE (AIR DIFFICULT TO EXHALE,");
 puts("        CAN MOVE SHORT DISTANCES,");
 puts("         BUT THEN MUST REST)");
 puts("3 - SEVERE (CANNOT GET ENOUGH AIR,");
 puts("       CANNOT MOVE AROUND)");
 puts("");
 if (sc1==0) {
  puts("ENTER YOUR SCORE: "); sc1=getch(); if ((sc1<48)||(sc1>51)) sc1=0; }
 else {
  printf("YOU HAVE ENTERED %c.\n",sc1);
  puts ("TO CONFIRM YOUR CHOICE");
```

FILE NO. A31572-A - 070050.0864

```
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
do {
 clrscr();
 puts("");
 puts("LIMITATION OF PHYSICAL ACTIVITY");
 puts("");
 puts("0 - NONE");
 puts("1 - MILD");
 puts("2 - MARKED");
 puts("");
 if (sc1==0) {
 puts("ENTER YOUR SCORE: "); sc1=getch(); if ((sc1<48)||(sc1>50)) sc1=0; }
 else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
do {
 clrscr();
 puts("");
 puts("ASTMA MEDICATION");
 puts("");
 puts("0 - AS USUAL");
 puts("1 - SLIGHTLY INCREASED DOSAGE");
 puts("2 - SIGNIFICANTLY INCREASED DOSAGE");
 puts("   OR USE OF ANOTHER DRUG");
 puts("");
 if (sc1==0) {
```

- 54 -

FILE NO. A31572-A - 070050.0864

```
 puts("ENTER YOUR SCORE: "); sc1=getch(); if ((sc1<48)||(sc1>50)) sc1=0; }
else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
do {
 clrscr();
 puts("HAVE YOU EXPERIENCED TODAY FACTORS");
 puts("THAT MAY EXACERBATE ASTHMA:");
 puts(" WEATHER CHANGES, ALLERGENS,");
 puts(" AIR POLLUTANTS, SULFUR DIOXIDE,");
 puts(" RESPIRATORY INFECTIONS,");
 puts(" UNUSUAL FOODS, ADDITIVES, DRUGS,");
 puts(" EXTREME EMOTIONAL EXPRESSION,");
 puts(" EXERCISE AND HYPERVENTILATION, ETC.");
 puts("");
 puts("0 - NO");
 puts("1 - YES");
 puts("");
 if (sc1==0) {
 puts("ENTER YOUR SCORE: "); sc1=getch(); if ((sc1<48)||(sc1>49)) sc1=0; }
else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

sc1=sc2=0;
do {
 clrscr();
 puts("WHAT IS YOUR OVER-ALL ESTIMATE");
```

- 55 -

FILE NO. A31572-A - 070050.0864

```
puts("OF ASTHMA SYMPTOMS TODAY:");
puts("");
puts("0 - NO SYMPTOMS");
puts("1 - MILD SYMPTOMS");
puts("2 - MODERATE SYMPTOMS");
puts("3 - SEVERE SYMPTOMS");
puts("");
if (sc1==0) {
 puts("ENTER YOUR SCORE: "); sc1=getch(); if ((sc1<48)||(sc1>51)) sc1=0; }
else {
 printf("YOU HAVE ENTERED %c.\n",sc1);
 puts ("TO CONFIRM YOUR CHOICE");
 printf("PLEASE ENTER %c AGAIN:",sc1);
 sc2=getch(); if (sc1!=sc2) sc1=sc2=0; }
}
while (sc2==0);
*scr++=sc1;

*scr=0;
}                       */
/*
void prn_status(AUX_MODE *mode, int port)
{
int blen;
aux_stat(mode, port);
switch (mode->baud) {
    case 0: blen=5;  break;
    case 1: blen=6;  break;
    case 2: blen=7;  break;
    case 3: blen=8;  break;
    default: blen=8; break;
};
printf(
"\nCOM%1d status         char length: %d      #stop-bits : %d\n"
"parity control : %d    parity fixation : %d    break status : %d\n"
"status bit : %d        speed : %d\n",
port,blen, mode->ctl_aux.ctl_word.stop+1, mode->ctl_aux.ctl_word.parity,
mode->ctl_aux.ctl_word.stuck_parity, mode->ctl_aux.ctl_word.en_break_ctl,
mode->ctl_aux.ctl_word.dlab, (unsigned long)mode->baud);
}
```

FILE NO. A31572-A - 070050.0864

```
*/ void aStrOut(char *s)
{
char *str;
str=s; while (*str) {aux_outp(*str,mCOM); str++;}
} int Resp(char *message,char *rsp,int waitSec)
{
time_t ss;
char *mssg;
unsigned status_reg, base_adr;
base_adr=def_base_adr(mCOM); status_reg=base_adr+LSR_N;
ss=time(NULL)+waitSec; mssg=message; //printf("%x %s\n",base_adr,rsp);
aStrOut(message);
do {
  while(((inp(status_reg)&1)==0)&&(ss>time(NULL)));
  if (ss<time(NULL)) {*mssg=0; return(0);}
          //{printf("Communication error."); exit(0);}
  *mssg++=inp(base_adr); *mssg=0; }
while (strstr(message,rsp)==NULL);
return(1);
} void decrypt(char *s)
{
int z,i;
z=-10; for (i=0;i<strlen(s);i++) s[i]=s[i]-z++;
}
        /*
void grDayScore(char *SS)
{
int Qn;
char ch, *c, *c1, s1[512];
char Tag[]="None      Severe";
char mTg[]="Low        High";
char fTg[]="";
int ss[10]; //Qn
int gdriver = DETECT, gmode, errorcode;
```

FILE NO. A31572-A - 070050.0864

```
int left,top,right,bottom,ll,l,r,nq,i;
FILE *f;
char ass[]="Please assess the symptom's strength:";
char Ndr[]="Please assess the drug consumption:";
char Nbr[]="Please assess use of bronchodilator:";

Qn=10;
initgraph(&gdriver, &gmode, ""); errorcode = graphresult();
if (errorcode != grOk)  // an error occurred
   {
     printf("Graphics error: %s\n", grapherrormsg(errorcode));
     printf("Press any key to halt:");
     getch();
     exit(1); // terminate with an error code
   }
left = 300; right = left+300;
top = 90; bottom = top+30;

nq=0; for (i=0;i<Qn;i++) ss[i]=left; ss[Qn-1]=0;

do {
  cleardevice(); rectangle(0,0,639,199);

settextstyle(DEFAULT_FONT, HORIZ_DIR, 1);
  outtextxy(85, bottom+55,
  "Use \"+\",\"-\", and left and right arrows to fill in the bar");
  outtextxy(135, bottom+65,
  "Use up and down arrows to browse the diary");

settextstyle(DEFAULT_FONT, HORIZ_DIR, 3);
  switch (nq) {
  case 0: outtextxy(10, top, "Wheezing"); break;
  case 1: outtextxy(10, top-15, "Chest");
       outtextxy(10, top+15,"Tightness");
       break;
  case 2: outtextxy(10, top-15,"Shortness");
       outtextxy(10, top+15,"of Breath");
       break;
  case 3: outtextxy(10, top, "Coughing"); break;
  case 4: outtextxy(10, top, "Sputum"); break;
```

FILE NO. A31572-A - 070050.0864

```
case 5: outtextxy(10, top-25, "Limitation");
    outtextxy(10, top, "of physical");
    outtextxy(10, top+25, "activity"); break;
case 6: outtextxy(10, top-25, "Over-all");
    outtextxy(10, top, "estimate");
    outtextxy(10, top+25, "of asthma"); break;
case 7: outtextxy(10, top-25, "Exposure");
    outtextxy(10, top, "to asthma");
    outtextxy(10, top+25, "triggers"); break;
case 8: outtextxy(10, top-35, "Over-all");
    outtextxy(10, top-12, "use of");
    outtextxy(10, top+12, "asthma");
    outtextxy(10, top+35, "medications"); break;
case 9: outtextxy(10, top-25, "Daytime");
    outtextxy(10, top, "reliever");
    outtextxy(10, top+25, "use"); break;
} ll=ss[nq];
rectangle(left,top,right,bottom);

settextstyle(DEFAULT_FONT, HORIZ_DIR, 2);
if (nq<8) {c1=ass; c=Tag;}
else
if (nq==8) {c1=Ndr; c=mTg;} else {c1=Nbr; c=fTg;}
outtextxy(20,10,c1); outtextxy(left, top-22, c);

if (nq==9) {
  sprintf(s1,"%d",ll); outtextxy(left+140, top+8, s1);
  do {
  ch=getch();
  if (ch=='+') {
   setfillstyle(SOLID_FILL,BLACK);
   bar(left+1,top+1,right-1,bottom-1); setfillstyle(SOLID_FILL,WHITE);
   sprintf(s1,"%d",++ll); outtextxy(left+140, top+8, s1); }
  if (ch=='-') {
   ll--; if (ll<0) ll=0; setfillstyle(SOLID_FILL,BLACK);
   bar(left+1,top+1,right-1,bottom-1); setfillstyle(SOLID_FILL,WHITE);
   sprintf(s1,"%d",ll); outtextxy(left+140, top+8, s1); }
  if (ch==0) {
```

FILE NO. A31572-A - 070050.0864

```
    ch=getch();
    if (ch==80) {ss[nq++]=ll; break;}
    if (ch==72) {ss[nq--]=ll; if (nq<0) nq=0; break;}
    if (ch==0x4D) {
     setfillstyle(SOLID_FILL,BLACK);
      bar(left+1,top+1,right-1,bottom-1); setfillstyle(SOLID_FILL,WHITE);
      sprintf(s1,"%d",++ll); outtextxy(left+140, top+8, s1); }
    }
    if (ch==0x4B) {
    ll--; if (ll<0) ll=0; setfillstyle(SOLID_FILL,BLACK);
     bar(left+1,top+1,right-1,bottom-1); setfillstyle(SOLID_FILL,WHITE);
     sprintf(s1,"%d",ll); outtextxy(left+140, top+8, s1); }
   }
   while (1);
   continue;
 } bar(left,top,ll,bottom);
 do {
  ch=getch();
  if (ch=='+') if (ll<right) {ll++; line(ll,top,ll,bottom);}
  if (ch=='-') {
    if ((ll!=left)&&(ll!=right))
    {setcolor(BLACK); line(ll,top+1,ll,bottom-1); setcolor(WHITE);}
    if (ll>left) ll--; }
  if (ch==0) {
    ch=getch();
    if (ch==80) {ss[nq++]=ll; break;}
    if (ch==72) {ss[nq--]=ll; if (nq<0) nq=0; break;}
    if (ch==0x4D) {
     ll+=10; if (ll>right) ll=right; bar(left,top,ll,bottom); }
    if (ch==0x4B) {
     r=ll; if (r==left) r=left+1; if (r==right) r=right-1;
     ll-=10; if (ll<left) ll=left; l=ll+1;
     if (l==left) l=left+1; if (l==right) l=right-1;
     setfillstyle(SOLID_FILL,BLACK);
     bar(l,top+1,r,bottom-1); setfillstyle(SOLID_FILL,WHITE); }
  }
 }
```

- 60 -

FILE NO. A31572-A - 070050.0864

```
    while(1);
}
while (nq<Qn);

closegraph();

c=SS; *c++='E';
for (i=0;i<Qn-1;i++) {
    sprintf(s1,"%5.0f",100.0*(ss[i]-left)/(right-left));
    *c++=atoi(s1)+35;
}
*c++=ss[Qn-1]+35; *c='\0';

//for (i=0;i<10;i++) printf("%d %d\n",ss[i],SS[i+1]-35);

}         */
/*
void grNightScore(char *SS)
{
int Qn;
char ch, *c, *c1, s1[512];
char Tag[]="No      Severe";
char fTg[]="";
int ss[3]; //Qn
int gdriver = DETECT, gmode, errorcode;
int left,top,right,bottom,ll,l,r,nq,i;
double w;
FILE *f;
char ass[]="Please assess how you slept today:";
char Nbr[]="Please assess use of bronchodilator:";

Qn=3;
initgraph(&gdriver, &gmode, ""); errorcode = graphresult();
if (errorcode != grOk)  // an error occurred
  {
    printf("Graphics error: %s\n", grapherrormsg(errorcode));
    printf("Press any key to halt:");
    getch();
    exit(1); // terminate with an error code
  }
```

FILE NO. A31572-A - 070050.0864

```
left = 300; right = left+300;
top = 90; bottom = top+30;

nq=0; ss[0]=left; for (i=1;i<Qn;i++) ss[i]=0;

do {
cleardevice(); rectangle(0,0,639,199);

settextstyle(DEFAULT_FONT, HORIZ_DIR, 1);
outtextxy(85, bottom+55,
"Use \"+\",\"-\", and left and right arrows to fill in the bar");
outtextxy(135, bottom+65,
"Use up and down arrows to browse the diary");

settextstyle(DEFAULT_FONT, HORIZ_DIR, 3);
switch (nq) {
case 0: outtextxy(10, top-25, "Disturbance");
    outtextxy(10, top, "of sleep");
    outtextxy(10, top+25, "by asthma"); break;
case 1: outtextxy(10, top-25, "Number of");
    outtextxy(10, top, "awakening");
    outtextxy(10, top+25, "by asthma"); break;
case 2: outtextxy(10, top-25, "Nighttime");
    outtextxy(10, top, "reliever");
    outtextxy(10, top+25, "use"); break;
} ll=ss[nq];
rectangle(left,top,right,bottom);

settextstyle(DEFAULT_FONT, HORIZ_DIR, 2);
if (nq==0) {c1=ass; c=Tag;}
else if (nq==1) {c1=ass; c=fTg;}
else {c1=Nbr; c=fTg;};
outtextxy(20,10,c1); outtextxy(left, top-22, c);

if (nq>0) {
  sprintf(s1,"%d",ll); outtextxy(left+140, top+8, s1);
  do {
  ch=getch();
```

- 62 -

FILE NO. A31572-A - 070050.0864

```
  if (ch=='+') {
   setfillstyle(SOLID_FILL,BLACK);
   bar(left+1,top+1,right-1,bottom-1); setfillstyle(SOLID_FILL,WHITE);
   sprintf(s1,"%d",++ll); outtextxy(left+140, top+8, s1); }
  if (ch=='-') {
   ll--; if (ll<0) ll=0; setfillstyle(SOLID_FILL,BLACK);
   bar(left+1,top+1,right-1,bottom-1); setfillstyle(SOLID_FILL,WHITE);
   sprintf(s1,"%d",ll); outtextxy(left+140, top+8, s1); }
  if (ch==0) {
   ch=getch();
   if (ch==80) {ss[nq++]=ll; break;}
   if (ch==72) {ss[nq--]=ll; if (nq<0) nq=0; break;}
   if (ch==0x4D) {
    setfillstyle(SOLID_FILL,BLACK);
    bar(left+1,top+1,right-1,bottom-1); setfillstyle(SOLID_FILL,WHITE);
    sprintf(s1,"%d",++ll); outtextxy(left+140, top+8, s1); }
   }
   if (ch==0x4B) {
   ll--; if (ll<0) ll=0; setfillstyle(SOLID_FILL,BLACK);
   bar(left+1,top+1,right-1,bottom-1); setfillstyle(SOLID_FILL,WHITE);
   sprintf(s1,"%d",ll); outtextxy(left+140, top+8, s1); }
  }
  while (1);
  continue;
 } bar(left,top,ll,bottom);
 do {
  ch=getch();
  if (ch=='+') if (ll<right) {ll++; line(ll,top,ll,bottom);}
  if (ch=='-') {
   if ((ll!=left)&&(ll!=right))
    {setcolor(BLACK); line(ll,top+1,ll,bottom-1); setcolor(WHITE);}
   if (ll>left) ll--;}
  if (ch==0) {
   ch=getch();
   if (ch==80) {ss[nq++]=ll; break;}
   if (ch==72) {ss[nq--]=ll; if (nq<0) nq=0; break;}
   if (ch==0x4D) {
```

FILE NO. A31572-A - 070050.0864

```
    ll+=10; if (ll>right) ll=right; bar(left,top,ll,bottom); }
    if (ch==0x4B) {
    r=ll; if (r==left) r=left+1; if (r==right) r=right-1;
    ll-=10; if (ll<left) ll=left; l=ll+1;
    if (l==left) l=left+1; if (l==right) l=right-1;
    setfillstyle(SOLID_FILL,BLACK);
    bar(l,top+1,r,bottom-1); setfillstyle(SOLID_FILL,WHITE); }
  }
 }
 while(1);
 }
 while (nq<Qn);

closegraph();

c=SS; *c++='M';
 for (i=0;i<1;i++) {
     sprintf(s1,"%5.0f",100.0*(ss[i]-left)/(right-left));
     *c++=atoi(s1)+35;
 }
 for (i=1;i<Qn;i++) *c++=ss[i]+35; *c='\0';

//for (i=0;i<3;i++) printf("%d %d\n",ss[i],SS[i+1]-35); exit(0);

}         */ void FVChelp(void)
{
clrscr();
  // 123456789012345678901234567890123456789
  puts("1. Take a deep breath, as much as you");
  puts("possibly can, until you cannot hold");
  puts("anymore (keep spirometer away from your");
  puts("mouth during this step).");
  puts("2. Place the mouthpiece in your mouth");
  puts("with your teeth around the outside, and");
  puts("close your lips tightly around it.");
  puts("3. Blow out, as hard and as fast as");
  puts("possible, try to force all the air you");
  puts("can from your lungs, try to keep");
```

FILE NO. A31572-A - 070050.0864

```c
puts("exhaling as long as possible (at least");
puts("6 seconds).");
puts("4. Breathe in as deeply and as fast as");
puts("possible.\n");
printf("     PRESS ANY KEY TO CONTINUE"); getch();
} void doFVC(int ntst)
{
clrscr();
  // 12345678901234567890123456789012345678 90
  printf("\n     SPIROMETRY TEST #%d\n\n",ntst+1);
puts("1. Switch off/on the spirometer.\n");
printf("2. Push the \"<%c%c\" button on the\n",196,217);
puts("spirometer several times until the");
puts("message \"PERFORM FVC TEST\" appears.\n");
puts("3. Perform the test and wait about 30");
puts("seconds until the spirometer beeps.\n");
printf("4. Push the \"<%c%c\" button on the\n",196,217);
puts("spirometer and wait until the data is");
printf("being transmitted (about 1 minute).");
//puts(" an acknowledge message is received.\n");
} void showFVC() //(char pn[29][15], float pv[29][3])
{
int i,p1,p2;

/*zoom to 80x25*/
asm {  MOV AH,0xD0
       MOV AL, 2
       INT 0x10  }
/*zoom to 64x18*/
asm {  MOV AH,0xD0
       MOV AL, 0x80
       INT 0x10  }
clrscr();
//puts("_____
   ");
printf("%-12s%6s%6s%4s  |  %-12s%6s%6s%4s\n",
```

FILE NO. A31572-A - 070050.0864

```
"Parameter","Pred","Act","%","Parameter","Pred","Act","%");
puts("_____
___");
for (i=0;i<14;i++) {
    if (i<6) p1=i; else p1=i+1; p2=15+i;
    printf("%-12s %5.1f %5.1f %3d   |   %-12s %5.1f %5.1f %3d\n",
    parnam[p1],parval[p1][0],parval[p1][1],(int)(parval[p1][2]+0.5),
    parnam[p2],parval[p2][0],parval[p2][1],(int)(parval[p2][2]+0.5));
}
printf("\n          TO CONTINUE - PRESS ANY BUTTON"); getch();
/*zoom to 80x25*/
asm {   MOV AH,0xD0
        MOV AL, 2
        INT 0x10   }
/*zoom to 40x16*/
asm {   MOV AH,0xD0
        MOV AL, 0x84
        INT 0x10   }
} void drawFVC() //(int MX[144], int MI[144])
{
int i, x, YM;
char str[8];
int gdriver = DETECT, gmode, errorcode; initgraph(&gdriver, &gmode, "");
YM=getmaxy(); settextstyle(DEFAULT_FONT,VERT_DIR,1);
outtextxy(30,YM-75,"F[l/s]"); outtextxy(265,YM-195,"V[l]");
line(40,YM-25,460,YM-25); line(250,YM-25,250,YM-170);
for (i=1;i<15;i++) {
    sprintf(str,"%3d",i);
    outtextxy(250-i*15+6,YM-20,str); outtextxy(250+i*15+6,YM-20,str);
    line(250-i*15,YM-23,250-i*15,YM-27);
    line(250+i*15,YM-23,250+i*15,YM-27);
}
for (i=1;i<7;i++) {
    sprintf(str,"%d",i);
    if (i % 2) outtextxy(250+14,YM-29-24*i,str);
    line(248,YM-25-24*i,252,YM-25-24*i);
}
for (i=0;i<143;i++) line(250-MX[i],YM-26-i,250-MX[i+1],YM-26-(i+1));
```

FILE NO. A31572-A - 070050.0864

```
for (x=143;x>0;x--) if (MI[x]>0) break; if (x==143) x--;
for (i=0;i<x+1;i++) line(250+MI[i],YM-26-i,250+MI[i+1],YM-26-(i+1));
outtextxy(480,YM-195,"TO CONTINUE -");
outtextxy(490,YM-195,"PRESS ANY BUTTON");
getch(); closegraph();
} void drawPnt(int x, int y)
{
int i,j;
for (i=x-1;i<=x+1;i++) for (j=y-1;j<=y+1;j++) putpixel(i,j,WHITE);
} void trends(int Nm)//(char pn[29][15],float pv[29][3],float bv[29][120],int Nm)
{
int i,x,j,lx,ly,x0,y0,x1,y1,Y0,Dx,lm=55,rm=50,um=8,dm=3;
float val[trLen],norm,minval,maxval,mk,mval;
char str[8];
int gdriver = DETECT, gmode, errorcode, Npnt, pnum;

pickPar:
clrscr();
for (i=0;i<14;i++) {
    if (i<6) x0=i; else x0=i+1; x1=15+i;
    printf("%3d. %-12s  %3d. %-12s\n",x0+1,parnam[x0],x1+1,parnam[x1]);
}
printf("\nENTER PARAMETER NUMBER OR 0 TO EXIT: "); scanf("%3s",str);
pnum=atoi(str); if ((pnum<1)||(pnum>29)||(pnum==7)) return; pnum--;

if (Nm<trLen) {
    Npnt=Nm+1; for (i=0;i<Npnt;i++) val[i]=valbuf[pnum][i];
}
else {
    Npnt=trLen; x=Nm%trLen;
    for (i=x+1;i<Npnt;i++) val[i-(x+1)]=valbuf[pnum][i];
    for (i=0;i<x+1;i++) val[i+(trLen-1-x)]=valbuf[pnum][i];
} norm=parval[pnum][0]; minval=35000; maxval=0;
for (i=0;i<Npnt;i++) {
```

FILE NO. A31572-A - 070050.0864

```
    if (val[i]<minval) minval=val[i]; if (val[i]>maxval) maxval=val[i];
}
if (norm<minval) minval=norm; if (norm>maxval) maxval=norm;

initgraph(&gdriver, &gmode, "");
lx=getmaxx()-lm-rm; ly=getmaxy()-um-dm; Y0=getmaxy()-dm; Dx=lx/(Npnt+1);
line(lm,Y0,getmaxx()-rm,Y0); line(lm,Y0,lm,um);
outtextxy(lm,1,parnam[pnum]);

/*max-min=ly model
mk=ly/(maxval-minval); mval=minval; */

/*min%max=%ly model*/
mk=ly/maxval; mval=minval/2;

x0=lm+Dx; y0=Y0-(int)((val[0]-mval)*mk+0.5); drawPnt(x0,y0);
for (i=1;i<Npnt;i++) {
    x1=lm+(i+1)*Dx; y1=Y0-(int)((val[i]-mval)*mk+0.5); drawPnt(x1,y1);
    line(x0,y0,x1,y1); x0=x1; y0=y1;
}
x1=getmaxx()-rm; y1=Y0-(int)((norm-mval)*mk+0.5); line(lm,y1,x1,y1);
sprintf(str,"%5.1f",norm); outtextxy(x1+2,y1-4,str);

x=10; j=ly/x;
for (i=0;i<x;i++) {
    y0=Y0-(i+1)*j; line(lm-2,y0,lm+2,y0);
    sprintf(str,"%5.1f",mval+(i+1)*j/mk); outtextxy(8,y0-4,str);
} getch(); closegraph(); goto pickPar;
} void PtMsg(char *Msg)
{
char s[80];

while (kbhit()) getch();
clrscr(); strcpy(Msg,"{*");
    // 123456789012345678901234567890123456789O
puts("If you would like to send a message to");
```

FILE NO. A31572-A - 070050.0864

```
puts("your doctor, please enter it now.");
puts("At the end of your message you should");
puts("push <Enter> twice.");
puts("TO SKIP THIS OPTION - PUSH <ENTER> NOW.");

while (strlen(Msg)<395) {
  gets(s);
  if ((*s==0)||(strlen(Msg)+strlen(s)>395)) {strcat(Msg,"*}"); return;}
  strcat(Msg,s); strcat(Msg,"\n");
}
} void showMsg(char *Msg)
{
clrscr();
puts(Msg); puts("");
printf("  TO CONTINUE - PLEASE PUSH ANY BUTTON"); getch();
}
```

FILE NO. A31572-A - 070050.0864 getpft

```c
#include <stdio.h>      /* start with par=wrk_dir/ */
#include <stdlib.h>     /* ex:  /home/homepft/   */
#include <string.h>
#include <sys/types.h>
#include <time.h>
include <memory.h> float StoF(char *str);
char codeASC(int val);
char *parDim(int i);
void test_hl7(char *HL7msg, char *wrkDir, char *AcsNum);
void repply(char *address, char *subject, char *message);

void main(int argc, char **argv)
{
char parHL7[97][55]={
"47646^HOME FVC DETERMINATION",
"47648^HOME FEV0.5 DETERMINATION",
"47650^HOME FEV0.5/FVC% DETERMINATION",
"47652^HOME FEV0.75 DETERMINATION",
"47654^HOME FEV0.75/FVC% DETERMINATION",
"47656^HOME FEV1 DETERMINATION",
"47658^HOME FEV1/VC% DETERMINATION",
"47660^HOME FEV1/FVC% DETERMINATION",
"47662^HOME FEV1/PEF DETERMINATION",
"47664^HOME FEV3 DETERMINATION",
"47666^HOME FEV3/FVC% DETERMINATION",
"47668^HOME PEF DETERMINATION",
"47682^HOME FEF25-75% DETERMINATION",
"47670^HOME FEF25-75/FVC% DETERMINATION",
"47684^HOME FEF75-85% DETERMINATION",
"47686^HOME FEF0.2-1.2 DETERMINATION",
"47672^HOME FEF25% DETERMINATION",
"47674^HOME FEF50% DETERMINATION",
"47676^HOME FEF75% DETERMINATION",
"47678^HOME FMFT DETERMINATION",
"47680^HOME FET DETERMINATION",
"47688^HOME MVV IND DETERMINATION",
```

FILE NO. A31572-A - 070050.0864

"47690^HOME FIVC DETERMINATION",
"47692^HOME FIVC/FVC% DETERMINATION",
"47694^HOME PIF DETERMINATION",
"47696^HOME FIF25% DETERMINATION",
"47698^HOME FIF50% DETERMINATION",
"47700^HOME FIF75% DETERMINATION",
"47702^HOME FIF50/FEF50% DETERMINATION",
"47704^HOME FEV CURVE DETERMINATION",
"47706^HOME FIV CURVE DETERMINATION",
"47708^HOME SYNDROMAL INTERPRETATION DETERMINATION",
"47710^HOME FVC PREDICTED VALUE",
"47712^HOME FEV0.5 PREDICTED VALUE",
"47714^HOME FEV0.5/FVC% PREDICTED VALUE",
"47716^HOME FEV0.75 PREDICTED VALUE",
"47718^HOME FEV0.75/FVC% PREDICTED VALUE",
"47720^HOME FEV1 PREDICTED VALUE",
"47722^HOME FEV1/VC% PREDICTED VALUE",
"47724^HOME FEV1/FVC% PREDICTED VALUE",
"47726^HOME FEV1/PEF PREDICTED VALUE",
"47728^HOME FEV3 PREDICTED VALUE",
"47730^HOME FEV3/FVC% PREDICTED VALUE",
"47732^HOME PEF PREDICTED VALUE",
"47734^HOME FEF25-75% PREDICTED VALUE",
"47736^HOME FEF25-75/FVC% PREDICTED VALUE",
"47738^HOME FEF75-85% PREDICTED VALUE",
"47740^HOME FEF0.2-1.2 PREDICTED VALUE",
"47742^HOME FEF25% PREDICTED VALUE",
"47744^HOME FEF50% PREDICTED VALUE",
"47746^HOME FEF75% PREDICTED VALUE",
"47748^HOME FMFT PREDICTED VALUE",
"47750^HOME FET PREDICTED VALUE",
"47752^HOME MVV IND PREDICTED VALUE",
"47754^HOME FIVC PREDICTED VALUE",
"47756^HOME FIVC/FVC% PREDICTED VALUE",
"47758^HOME PIF PREDICTED VALUE",
"47760^HOME FIF25% PREDICTED VALUE",
"47762^HOME FIF50% PREDICTED VALUE",
"47764^HOME FIF75% PREDICTED VALUE",
"47766^HOME FIF50/FEF50% PREDICTED VALUE",
"47768^HOME PERCENTAGE FVC OF PREDICTED VALUE",

FILE NO. A31572-A - 070050.0864

"47770^HOME PERCENTAGE FEV0.5 OF PREDICTED VALUE",
"47772^HOME PERCENTAGE FEV0.5/FVC% OF PREDICTED VALUE",
"47774^HOME PERCENTAGE FEV0.75 OF PREDICTED VALUE",
"47776^HOME PERCENTAGE FEV0.75/FVC% OF PREDICTED VALUE",
"47778^HOME PERCENTAGE FEV1 OF PREDICTED VALUE",
"47780^HOME PERCENTAGE FEV1/VC% OF PREDICTED VALUE",
"47782^HOME PERCENTAGE FEV1/FVC% OF PREDICTED VALUE",
"47784^HOME PERCENTAGE FEV1/PEF OF PREDICTED VALUE",
"47786^HOME PERCENTAGE FEV3 OF PREDICTED VALUE",
"47788^HOME PERCENTAGE FEV3/FVC% OF PREDICTED VALUE",
"47790^HOME PERCENTAGE PEF OF PREDICTED VALUE",
"47792^HOME PERCENTAGE FEF25-75% OF PREDICTED VALUE",
"47794^PERCENTAGE HOME FEF25-75/FVC% OF PREDICTED VALUE",
"47796^PERCENTAGE HOME FEF75-85% OF PREDICTED VALUE",
"47798^HOME PERCENTAGE FEF0.2-1.2 OF PREDICTED VALUE",
"47800^HOME PERCENTAGE FEF25% OF PREDICTED VALUE",
"47802^HOME PERCENTAGE FEF50% OF PREDICTED VALUE",
"47804^HOME PERCENTAGE FEF75% OF PREDICTED VALUE",
"47806^HOME PERCENTAGE FMFT OF PREDICTED VALUE",
"47808^HOME PERCENTAGE FET OF PREDICTED VALUE",
"47810^HOME PERCENTAGE MVV IND OF PREDICTED VALUE",
"47812^HOME PERCENTAGE FIVC OF PREDICTED VALUE",
"47814^HOME PERCENTAGE FIVC/FVC% OF PREDICTED VALUE",
"47816^HOME PERCENTAGE PIF OF PREDICTED VALUE",
"47818^HOME PERCENTAGE FIF25% OF PREDICTED VALUE",
"47820^HOME PERCENTAGE FIF50% OF PREDICTED VALUE",
"47822^HOME PERCENTAGE FIF75% OF PREDICTED VALUE",
"47824^HOME PERCENTAGE FIF50/FEF50% OF PREDICTED VALUE",
"47826^HOME TEST VARIABILITY",
"47828^HOME METHOD OF PREDICTED VALUE CALCULATION",
"47830^HOME NUMBER OF TEST ATTEMPTS",
"47832^HOME TESTING DEVICE",
"49893^TECHNICAL NOTES OF HOME SPIROMETRY",
"49889^HOME MORNING SCORE",
"49891^HOME EVENING SCORE"};
/*
MSH|^~\&|HOMEPFT|cucis|cis.uservice|cicsu9.phis|19910514104740||ORU^R01|199105
14104740|P|2.1||
PID|||3131313||SANDIEGO^CARMEN|||M|||||||||||
OBR|||XBCDEF1234567890^158|47639^Home Forced Vital Capacity

FILE NO. A31572-A - 070050.0864

```
Test^L^32506^Service
event^L|||19910513084800||||||||||||19910514104740|||F||||||sidelir^SIDELI^ROBERT^V||||
OBX|1|NM|46468^Home FVC determination^MED|0|4.19|LITER|||||
OBX|2|NM|46469^Home FVC predicted value^MED|0|4.92|LITER|||||
OBX|3|NM|46470^Home Percentage FVC of predicted value^MED|0|99|%|||||| */

FILE *f;
int i,j,y,k,l,m,z,A;
int Sc[10];
unsigned char ch;
float parval[29][3];
char s1[512],s2[512],s3[64],s4[64],ID[8],MRN[10],NAME[32],AccssN[18]="";
char hl7[10000];
unsigned char p[2000];
char *c=p, *c1, *c2;
char DATFRM[]="%04d%02d%02d%02d%02d%02d";
time_t Tp;
struct tm *tmP;
char **comlin=argv;
char wrkDir[64]="",Age[4],Height[8],Sex[2],Origin[16],transMode;
char PrePost[2],DrTime[10],SpTime[10];

if (argc>1) for (i=1;i<3;i++) sprintf(wrkDir,"%s",*comlin++);

gets(p); strcat(p,"\n");
if (strstr(p,"telnet")!=NULL) {       /*get telnet data*/
   do {gets(s1); strcat(s1,"\n"); strcat(p,s1);} while (*s1!='!');
   transMode='T'; }
else { /*j=0*/              /*get e-mail*/
   j=strlen(p); while ((i=getchar())!=EOF) p[j++]=(unsigned char)i; p[j]='\0';
   transMode='E';
} c=strstr(c,"HomePFT_ID:"); if (c==NULL) exit(0);
sscanf(c,"%s%s",s1,ID);
sprintf(s2,"%sPFT_IDtoMRN.lst",wrkDir); f=fopen(s2,"r");
do fscanf(f,"%s%s%s",s1,MRN,NAME); while ((feof(f)==0)&&(strcmp(s1,ID)!=0));
fclose(f); if (strcmp(s1,ID)!=0) exit(0);
c=strchr(c,'\n'); c++;
```

FILE NO. A31572-A - 070050.0864

```
sprintf(s2,"%ssendpft.hl7",wrkDir); f=fopen(s2,"w");
time(&Tp); tmP=localtime(&Tp);

/*MSH*/    /*s2-current date*/
sprintf(s2,DATFRM,tmP->tm_year+1900,tmP->tm_mon+1,tmP->tm_mday,tmP->tm_hou
r,tmP->tm_min,tmP->tm_sec);
strcpy(s1,"MSH!^~\\&!HOMEPFT!cucis!cis.uservice!cicsu9.phis!");
strcat(s1,s2); strcat(s1,"!!ORU^R01!");strcat(s1,s2); strcat(s1,"!P!2.1!!\r");
strcpy(hl7,s1);

/*PID*/
sprintf(s1,"PID!!!%s!!%s!!!M!!!!!!!!!!!!!\r",MRN,NAME);
strcat(hl7,s1);

/*OBR*/    /*s2-test date*/
sscanf(c,"%d%d%d%d%d%d%d",&y,&i,&j,&k,&l,&m); c=strchr(c,'\n'); c++;
sprintf(s2,DATFRM,y,i,j,k,l,m);
sprintf(AccssN,"%4d%c%c%c%c%c%c%+07s",y,codeASC(i),codeASC(j),codeASC(k),code
ASC(l),codeASC(m),ID);
strcpy(s1,"OBR!!!"); strcat(s1,AccssN); strcat(s1,
"^158!47639^Home Forced Vital Capacity Test^L^32506^Service event^L!!!");
strcat(s1,s2); strcat(s1,"!!!!!!!!!!!!!!!!"); strcat(s1,s2);
strcat(s1,"!!!F!!!!!!!!sidelir^SIDELI^ROBERT^V!!!!\r");
strcat(hl7,s1);

sscanf(c,"%s%s%s%s%s%s%s",Age,Height,Sex,Origin,PrePost,DrTime,SpTime);
c=strchr(c,'\n'); c++;

/*OBX*/
k=0;
/*variability*/
i=0; do s2[i++]=*c++; while (*c!='\n'); c++; s2[i]='\0';
sprintf(s1,"OBX!%d!ST!%s^MED!0!%s!!!!!!!\r",++k,parHL7[90],s2);
strcat(hl7,s1);

/*number of test attempts*/
sscanf(c,"%s",s2); c=strchr(c,'\n'); c++;
sprintf(s1,"OBX!%d!NM!%s^MED!0!%s!!!!!!!\r",++k,parHL7[92],s2);
strcat(hl7,s1);
```

FILE NO. A31572-A - 070050.0864

```
/*meth of calc*/
i=0; do s2[i++]=*c++; while (*c!='\n'); c++; s2[i]='\0';
sprintf(s1,"OBX!%d!ST!%s^MED!0!%s!!!!!!!\r",++k,parHL7[91],s2);
strcat(hl7,s1);

/*test device*/
sprintf(s1,"OBX!%d!ST!%s^MED!0!%s!!!!!!!\r",++k,parHL7[93],"V2120");
strcat(hl7,s1);

/*PFT parameters*/ /*28/29*/
for (i=0;i<29;i++) {
   sscanf(c,"%s%s%s",s2,s3,s4); c=strchr(c,'\n'); c++;
   parval[i][0]=StoF(s2); parval[i][1]=StoF(s3); parval[i][2]=StoF(s4);
   sprintf(s1,"OBX!%d!NM!%s^MED!0!%s!%s!!!!!!\r",++k,parHL7[i+32],s2,parDim(i));
   strcat(hl7,s1);
   sprintf(s1,"OBX!%d!NM!%s^MED!0!%s!%s!!!!!!\r",++k,parHL7[i],s3,parDim(i));
   strcat(hl7,s1);
   sprintf(s1,"OBX!%d!NM!%s^MED!0!%s!%s!!!!!!\r",++k,parHL7[i+61],s4,"%");
   strcat(hl7,s1);
}

/*syndromal interpret*/
i=0; do s2[i++]=*c++; while (*c!='\n'); c++; s2[i]='\0';
sprintf(s1,"OBX!%d!ST!%s^MED!0!%s!!!!!!!\r",++k,parHL7[31],s2);
strcat(hl7,s1);

/*graph-FEV*/
if (transMode=='T')
   for (i=0;i<144;i++) {sscanf(c,"%d",&z); c=strchr(c,'\n'); c++; s2[i]=z;}
else {for (i=0;i<144;i++) s2[i]=*c++; while(*c++!='\n');}
s2[i]='\0';
sprintf(s1,"OBX!%d!TX!%s^MED!0!%s %s %s %s %s %s %s!!!!!!!\r",
   ++k,parHL7[29],s2,Age,Height,Sex,Origin,PrePost,DrTime,SpTime);
strcat(hl7,s1);

/*graph-FIV*/
A=144+1;
if (transMode=='T') { /*will work only if M or E are def,o.w.-error*/
   for (i=0;i<144;i++) {sscanf(c,"%d",&z); c=strchr(c,'\n'); c++; s2[i]=z;}
   s2[144]=*c; if (*c=='M') j=3; else if (*c=='E') j=10; else j=0;
```

FILE NO. A31572-A - 070050.0864

```
    c=strchr(c,'\n'); c++;
    if (j>0) for (i=A;i<A+j;i++) {
      sscanf(c,"%d",&z); c=strchr(c,'\n'); c++; s2[i]=z; Sc[i-A]=z-35;}
  }
  else {
    for (i=0;i<144;i++) s2[i]=*c++;
    s2[144]=*c; if (*c=='M') j=3; else if (*c=='E') j=10; else j=0;
    c++; if (j>0) for (i=A;i<A+j;i++) {s2[i]=*c++; Sc[i-A]=z-35;}
  }
  s2[i]='\0';
  sprintf(s1,"OBX!%d!TX!%s^MED!0!%s!!!!!!!\r",++k,parHL7[30],s2);
  strcat(hl7,s1);

/*asthma score*/
  if (j==3) z=95; else z=96; strcpy(s2,"G");
  for (i=0; i<j; i++) {sprintf(s3," %d",Sc[i]); strcat(s2,s3);}
  sprintf(s1,"OBX!%d!TX!%s^MED!0!%s!!!!!!!\r",++k,parHL7[z],s2);
  strcat(hl7,s1);

/*tech info: age,height,sex,origin,PrePost,DrTime,SpTime,PtMsg*/
  if ((c1=strstr(c,"{*"))==NULL) strcpy(s2,"{**}");
  else if ((c2=strstr(c,"*}"))==NULL) strcpy(s2,"{**}");
  else {
    c=c1; c2++; i=0;
    while (c<=c2)
      if ((*c=='\n')||(*c=='\r'))
        {s2[i++]='<'; s2[i++]='B';s2[i++]='R';s2[i++]='>'; c++;}
      else s2[i++]=*c++;
    s2[i]='\0';
  }
  sprintf(s1,"OBX!%d!TX!%s^MED!0!%s %s %s %s %s %s
%s!!!!!!!\r",++k,parHL7[94],
  Age,Height,Sex,Origin,PrePost,DrTime,SpTime,s2);
  strcat(hl7,s1);

fputs(hl7,f); fclose(f);

sprintf(s1,"%s%s.PFT",wrkDir,AccssN);
  f=fopen(s1,"w"); /*c=strstr(p,"FVC:");*/ c=p; fputs(c,f); fclose(f);
```

FILE NO. A31572-A - 070050.0864

```
test_hl7(hl7,wrkDir,AccssN); /*
strcpy(s1,"hl7sap -s cis.uservice@cicst2.phis%/home/homepft/ciscomtab -i");
strcat(s1," /home/homepft/sendpft.hl7");
f=popen(s1,"r");
j=0; while ((i=fgetc(f))!=EOF) p[j++]=i; p[j]='\0';
pclose(f); */ if (transMode=='T') {      /*telnet repply*/
  printf("!MSG\n");
  printf("The test has been delivered and stored.\n");
  printf("!MSG\n"); }
else {           /*e-mail repply*/
  strcpy(s1,"cpmc1@radiomail.net");
  strcpy(s3,"The test has been successful!");
  strcpy(s2,"The test has been delivered and stored.");
  repply(s1,s3,s2); }
} char *parDim(int pnum) { /*28/29*/
switch (pnum) {
case 0:
case 1:return("LITER"); break;
case 2:return("%"); break;
case 3:return("LITER"); break;
case 4:return("%"); break;
case 5:return("LITER"); break;
case 6:
case 7:return("%"); break;
case 8:return("MIN"); break;
case 9:return("LITER"); break;
case 10:return("%"); break;
case 11:return("LITER/MIN"); break;
case 12:return("LITER/SEC"); break;
case 13:return("%"); break;
case 14:
case 15:
case 16:
case 17:
case 18:return("LITER/SEC"); break;
case 19:
```

FILE NO. A31572-A - 070050.0864

```
case 20:return("SEC"); break;
case 21:return("LITER/MIN"); break;
case 22:return("LITER"); break;
case 23:return("%"); break;
case 24:return("LITER/MIN"); break;
case 25:
case 26:
case 27:return("LITER/SEC"); break;
case 28:return("%");
}
} char codeASC(int val) {
if (val>35) return(val+61); else if (val>9) return(val+55); else return(val+48);
} float StoF(char *str) {
if (str[0]=='-') {str[0]='\0'; return(0.0);} else return(atoff(str));
} void test_hl7(char *hl7msg, char *wDir, char *AcsN)
{
int         a,i,k;
char        outmsg[32755];
unsigned short   outlength;
char        qry[10000];
char s[]="cis.uservice@cicst2.phis%";
char svc[256];
FILE *fRES;

i=k=0;
while(!k&&i<5) {
    k=0;
    outlength=32754; strcpy(qry,hl7msg); /*
    strcpy(svc,s); strcat(svc,wDir); strcat(svc,"ciscomtab"); */
    k=hl7sap("",qry,outmsg,&outlength);
    outmsg[outlength]='\0';
    if(!k) i++;
}
if(!k&&i==5) {
```

FILE NO. A31572-A - 070050.0864

```
    fprintf(stderr,"Failed on HL7SAP\n");
  }
for (i=0; i<strlen(outmsg);i++) {
   if(outmsg[i]=='\r') outmsg[i]='\n';} sprintf(svc,"%s%s.RES",wDir,AcsN); fRES=fopen(svc,"w");
fprintf(fRES,"%s\n",outmsg); fclose(fRES);
} void repply(char *email,char *sbjt,char *mg)
{
FILE *out;
char s[256];

sprintf(s,"mail %s",email); out=popen(s,"w");
fprintf(out,"~s%s\n",sbjt); fprintf(out,"%s\n\n\n",mg);
pclose(out);
}
```

FILE NO. A31572-A - 070050.0864 startpft

```c
#include <string.h>
#include <netdb.h>
#include <sys/types.h>
#include <unistd.h>
#include <netinet/in.h>
#include <stdio.h>
#include <stdlib.h>
include <sys/file.h> define MAX_ENTRIES 10000
define LF 10
define CR 13
define blen 133 typedef struct {
   char *name;
   char *val;
} entry;

char *makeword(char *line, char stop);
char *fmakeword(FILE *f, char stop, int *len);
char x2c(char *what);
void unescape_url(char *url);
void plustospace(char *str);

char *gettxt(char *msgpnt,char *txtdat,char *ptrn);
void test_hl7(char *m,char *mrn);

void getalerts(char *MRN);

main(int argc, char *argv[]) {
   entry entries[MAX_ENTRIES];
   register int x,m=0;
   int cl;
char no_data[]="NO DATA FOUND";
char msg[32755];
char *c=msg;
```

FILE NO. A31572-A - 070050.0864

```
char s[512],s0[64],MRN[10];
int i,yr,mt,dy,hr,mn,sc,recnum;

printf("Content-type: text/html%c%c",10,10);

if(strcmp(getenv("REQUEST_METHOD"),"POST")) {
        printf("This script should be referenced with a METHOD of POST.\n");
        printf("If you don't understand this, see this ");
        printf("<A
HREF=\"http://www.ncsa.uiuc.edu/SDG/Software/Mosaic/Docs/fill-out-forms/overview.h
tml\">forms overview</A>.%c",10);
        exit(1);
    }
    if(strcmp(getenv("CONTENT_TYPE"),"application/x-www-form-urlencoded")) {
        printf("This script can only be used to decode form results. \n");
        exit(1);
    }
    cl = atoi(getenv("CONTENT_LENGTH"));

for(x=0;cl && (!feof(stdin));x++) {
        m=x;
        entries[x].val = fmakeword(stdin,'&',&cl);
        plustospace(entries[x].val);
        unescape_url(entries[x].val);
        entries[x].name = makeword(entries[x].val,'=');
    }
/*
    printf("<H1>Query Results</H1>");
    printf("You submitted the following name/value pairs:<p>%c",10);
    printf("<ul>%c",10);

for(x=0; x <= m; x++){
        printf("<li> <code>%s = %s</code>%c",entries[x].name,
            entries[x].val,10);
    }
    printf("</ul>%c",10);
    printf("\n<B>This is the end</B>");
*/ strcpy(MRN,entries[0].val);
```

FILE NO. A31572-A - 070050.0864

```
if (strcmp("alrt",entries[1].val)==0) {getalerts(MRN); exit(0);}

/*clean some memory*/
  for(x=0;x <= m; x++){
    free(entries[x].name);
    free(entries[x].val);
  } test_hl7(msg,MRN); printf("<BR>MRN = %s<BR>",MRN);
if (strstr(msg,no_data)!=NULL) {puts(no_data); exit(0);} printf(
"<FORM METHOD=\"POST\"
ACTION=\"http://www.cpmc.columbia.edu/homepages/finkelj/viewpft.cgi\">\n");
printf(
"<INPUT TYPE=\"hidden\" NAME=\"MRN\" VALUE=\"%s\">",MRN);
printf(
"<B> Please choose tests from the list </B><BR>\n");
printf(
"Ctrl-Click adds more than one item, Shift-Click selects a range of items.<BR>\n");
printf(
"<SELECT NAME=\"TestList\" MULTIPLE SIZE=\"8\">\n");

c=gettxt(c,s,"ROWS="); recnum=atoi(s);
for (i=0;i<recnum;i++) {
  c=gettxt(c,s,"OBR!!!"); s[16]='\0'; printf("<OPTION VALUE=\"%s\">",s);
  c=gettxt(c,s,"!!!!"); strncpy(s0,s+4,2); s0[2]='\0';
  printf("DATE=%s/",s0);
  strncpy(s0,s+6,2); s0[2]='\0'; printf("%s/",s0);
  strncpy(s0,s,4); s0[4]='\0'; printf("%s_____",s0);
  strncpy(s0,s+8,2); s0[2]='\0'; printf("TIME=%s:",s0);
  strncpy(s0,s+10,2); s0[2]='\0'; printf("%s:",s0);
  strncpy(s0,s+12,2); s0[2]='\0'; printf("%s\n",s0);
}
printf("</SELECT><BR><P>\n");
printf("<INPUT TYPE=\"SUBMIT\" VALUE=\" Submit \"\n");
printf("</FORM>\n");
}
```

FILE NO. A31572-A - 070050.0864

```
void getalerts(char *MRN)

{ char *ahost="cucis.cpmc.columbia.edu";

short inport=512;

char *user="homepft";

char *passwd="lungtest";

char cmdstr[128];

char *cmd=cmdstr;

int fd,count,j,i,z;

char buffer[BUFSIZ],p[32000],v[16];

char *c;

char parnam[29][20]={

"FVC","FEV.5","FEV.5/FVC%","FEV.75","FEV.75/FVC%","FEV1",

"FEV1/VC%","FEV1/FVC%","FEV1/PEF","FEV3","FEV3/FVC%","PEF"
,
    "FEF25-75%","FEF25-75/FVC","FEF75-85%","FEF.2-1.2","FEF25%",

"FEF50%","FEF75%","FMFT","FET","MVVind","FIVC","FIVC/FVC%",

"PIF","FIF25%","FIF50%","FIF75%","FIF50/FEF50%"};

float buff[blen];

float NIHPEF[3]={80,50,0};
```

FILE NO. A31572-A - 070050.0864

```
sprintf(cmdstr,"showalrt.exe %s",MRN);

fd=rexec(&ahost,inport,user,passwd,cmd,0); i=0;

while ((count=read(fd,buffer,BUFSIZ))>0)

/* fwrite(buffer,count,1,stdout); */
for (j=0;j<count;j++) p[i++]=buffer[j]; p[i]=0; c=p;
for (i=0;i<blen;i++) {sscanf(c,"%f",&buff[i]); c=strchr(c,'\n'); c++;} puts("<CENTER><H1>Web-based Asthma Monitor</H1>");

printf("<BR>MRN = %s<BR>",MRN);

puts("<FORM ACTION=\"cgitst.cgi\" METHOD=\"POST\">");

puts("<TABLE BORDER>");

puts("<CAPTION><FONT COLOR=\"#0000FF\">Alerts
Conditions</FONT></CAPTION>");

puts("<TR><TH>Parameter</TH><TH>% pred</TH>");

puts("<TH>% best</TH><TH>% last</TH><TH>% mean</TH>");

for (i=0;i<30;i++) { if (i<29) c=parnam[i]; else c="Diary Score";

printf("<TR><TH ALIGN=LEFT>%s</TH>\n",c);

for (z=0;z<4;z++) { if (buff[i*4+z]<999) sprintf(v,"%5.1f",buff[i*4+z]); else *v=0;

printf("<TD><INPUT TYPE=\"TEXT\" ");
printf("NAME=\"p%02d%d\" SIZE=\"10\" value=\"%s\"></TD>\n",i,z,v);
```

FILE NO. A31572-A - 070050.0864

```
  }
} puts("</TABLE><BR>");

puts("<TABLE BORDER>");

puts("<CAPTION><FONT COLOR=\"#0000FF\">NIH/NHLBI PEF
Alerts</FONT></CAPTION>");

puts("<TR><TH></TH><TH><FONT COLOR=\"#47A41E\">good
control</FONT></TH>");

puts("<TH><FONT COLOR=\"#F1A60A\">caution</FONT></TH>");

puts("<TH><FONT COLOR=\"#C91F16\">medical alert</FONT></TH>");

for (i=0;i<2;i++) { if (i) c="PEF L/min"; else c="% best";
  printf("<TR><TH ALIGN=LEFT>%s</TH>\n",c);

for (z=0;z<3;z++) { if (!i) sprintf(v,"%5.1f",NIHPEF[z]); else *v=0;

printf("<TD><INPUT TYPE=\"TEXT\" ");

printf("NAME=\"n%02d%d\" SIZE=\"10\" value=\"%s\"></TD>\n",i,z,v);

}
}
```

- 85 -

FILE NO. A31572-A - 070050.0864

```
puts("</TABLE><BR>");

puts("Post-bronchodilator PEF increase (%)");

puts("<INPUT TYPE=\"TEXT\" NAME=\"PostPre\" size=\"10\" value=\"20\"><BR>");

puts("Diurnal PEF variability (%)");
puts("<INPUT TYPE=\"TEXT\" NAME=\"DiaPEF\" size=\"10\"><BR>");

puts("NIH Guidelines alerts by computing device");

puts("<INPUT TYPE=\"CHECKBOX\" NAME=\"NIHAlrt\" VALUE=\"Yes\"><BR>");

puts("Alert by patient's new message");

puts("<INPUT TYPE=\"CHECKBOX\" NAME=\"PtMsgAlrt\"
VALUE=\"Yes\"><BR>");

puts("Compliance alert");

puts("<INPUT TYPE=\"TEXT\" NAME=\"ComplAlrt\">");

puts("missed days<BR>");

puts("Message for the patient<BR>");

puts("<TEXTAREA NAME=\"PhysMsg\" ROWS=\"8\"
COLS=\"50\"></TEXTAREA><BR>");

puts("<INPUT TYPE=\"SUBMIT\" VALUE=\"Submit new alerts\" SIZE=\"30\">");

puts("</FORM></CENTER>");
```

FILE NO. A31572-A - 070050.0864

```
} char *gettxt(char *msgpnt,char *txtdat,char *ptrn)
{
int i;
msgpnt=strstr(msgpnt,ptrn); msgpnt+=strlen(ptrn);
i=0; while (*msgpnt!='!') txtdat[i++]=*msgpnt++; txtdat[i]='\0';
return(msgpnt);
} void test_hl7(char *data,char *pID)
{
int yr,mt,dy,hr,mn,sc;
int a,i,k;
char qry_line_1_1[]="MSH!^~\\&!tst!cucis!cis.qservice!cicsl9.phis!19950125120000!!QRY!1 9950125120000!D!2.1!\"!";
char qry_line_2_1[]="\rQRD!19950125120000!R!I!finkelj!!!0!"; /*3131313*/
char qry_line_2_2[]="!RES!*!*!B";
char qry_line_3_1[]="\rQRF!*!19921104000000!19981231110700!SERVICE~AT~~ !95~57~55~*~~ ~UR~ ~*~*~*~*~158";
char           outmsg[32755],s[512];
unsigned short     outlength;
char           qry[1024]="",tmp_qry[10024]="";
FILE *f;
char svc[]="cis.qservice@cicst2.phis%ciscomtab";

sprintf(qry,"%s%s%s%s%s",
      qry_line_1_1,qry_line_2_1,pID,qry_line_2_2,qry_line_3_1);
  i=k=0;
  while(!k&&i<5) {
    k=0;
    outlength=32754;
    sprintf(tmp_qry,"%s",qry); sprintf(s,"%s","");
    k=hl7sap(s,tmp_qry,outmsg,&outlength);
    outmsg[outlength]='\0';
```

FILE NO. A31572-A - 070050.0864

```
    if(!k) i++;
  }
  if(!k&&i==5) {
    fprintf(stderr,"Failed on HL7SAP\n");
  }
for (i=0; i<strlen(outmsg);i++) {
  if(outmsg[i]=='\r') outmsg[i]='\n';
}
strcpy(data,outmsg);
}

/**/ void getword(char *word, char *line, char stop) {
  int x = 0,y;

for(x=0;((line[x]) && (line[x] != stop));x++)
     word[x] = line[x];

word[x] = '\0';
  if(line[x]) ++x;
  y=0;

while(line[y++] = line[x++]);
} char *makeword(char *line, char stop) {
  int x = 0,y;
  char *word = (char *) malloc(sizeof(char) * (strlen(line) + 1));

for(x=0;((line[x]) && (line[x] != stop));x++)
     word[x] = line[x];

word[x] = '\0';
  if(line[x]) ++x;
  y=0;

while(line[y++] = line[x++]);
  return word;
}
```

FILE NO. A31572-A - 070050.0864

```c
char *fmakeword(FILE *f, char stop, int *cl) {
  int wsize;
  char *word;
  int ll;

wsize = 102400;
  ll=0;
  word = (char *) malloc(sizeof(char) * (wsize + 1));

while(1) {
    word[ll] = (char)fgetc(f);
    if(ll==wsize) {
      word[ll+1] = '\0';
      wsize+=102400;
      word = (char *)realloc(word,sizeof(char)*(wsize+1));
    }
    --(*cl);
    if((word[ll] == stop) || (feof(f)) || (!(*cl))) {
      if(word[ll] != stop) ll++;
      word[ll] = '\0';
      return word;
    }
    ++ll;
  }
} char x2c(char *what) {
  register char digit;

digit = (what[0] >= 'A' ? ((what[0] & 0xdf) - 'A')+10 : (what[0] - '0'));
  digit *= 16;
  digit += (what[1] >= 'A' ? ((what[1] & 0xdf) - 'A')+10 : (what[1] - '0'));
  return(digit);
} void unescape_url(char *url) {
  register int x,y;

for(x=0,y=0;url[y];++x,++y) {
    if((url[x] = url[y]) == '%') {
```

FILE NO. A31572-A - 070050.0864

```
        url[x] = x2c(&url[y+1]);
        y+=2;
      }
    }
    url[x] = '\0';
} void plustospace(char *str) {
    register int x;

for(x=0;str[x];x++) if(str[x] == '+') str[x] = ' ';
} int rind(char *s, char c) {
    register int x;
    for(x=strlen(s) - 1;x != -1; x--)
        if(s[x] == c) return x;
    return -1;
} int getline(char *s, int n, FILE *f) {
    register int i=0;

while(1) {
        s[i] = (char)fgetc(f);

if(s[i] == CR)
            s[i] = fgetc(f);

if((s[i] == 0x4) || (s[i] == LF) || (i == (n-1))) {
            s[i] = '\0';
            return (feof(f) ? 1 : 0);
        }
        ++i;
    }
} void send_fd(FILE *f, FILE *fd)
{
    int num_chars=0;
```

FILE NO. A31572-A - 070050.0864

```
  char c;

while (1) {
    c = fgetc(f);
    if(feof(f))
      return;
    fputc(c,fd);
  }
}
```

FILE NO. A31572-A - 070050.0864

<u>viewpft</u>

```c
#include <stdio.h>
#include <stdlib.h>
include <sys/file.h>
#include <string.h>
#include <memory.h>
#include "gd.h"
#include "gdfonts.h"

#define MAX_ENTRIES 10000
define LF 10
define CR 13 typedef struct {
    char *name;
    char *val;
} entry;

char *makeword(char *line, char stop);
char *fmakeword(FILE *f, char stop, int *len);
char x2c(char *what);
void unescape_url(char *url);
void plustospace(char *str);

void test_hl7(char *m, char *AccssN);
char *gettxt(char *msgpnt,char *txtdat,char *ptrn);
void PtData(char *c);
void PtMsg(char *hl7msg);
void Score(char *c);
void convGRdt(char *msg, char *s, char *hl7code);
void CheckFls(char *filnam, char *AccssN);

char MRN[10];

main(int argc, char *argv[]) {
    entry entries[MAX_ENTRIES];
    register int x,m=0;
    int cl;
int i,z;
```

FILE NO. A31572-A - 070050.0864

```c
int MX[144],MX0[144],MI0[144],clr[10];
float parval[3][29],val;
FILE *out;
char s[256],s0[64],AccssN[32];
char msg[10000];
char *c1,*c=msg;
gdImagePtr im;
int black,white,red,blue;
char str[4];
char parnam[29][20]={
    "FVC","FEV.5","FEV.5/FVC%","FEV.75","FEV.75/FVC%","FEV1", "FEV1/VC%","FEV1/FVC%","FEV1/PEF","FEV3","FEV3/FVC%","PEF"
,
    "FEF25-75%","FEF25-75/FVC","FEF75-85%","FEF.2-1.2","FEF25%", "FEF50%","FEF75%","FMFT","FET","MVVind","FIVC","FIVC/FVC%",
    "PIF","FIF25%","FIF50%","FIF75%","FIF50/FEF50%"};

char parHL7[97][55]={
"47646^HOME FVC DETERMINATION",
"47648^HOME FEV0.5 DETERMINATION",
"47650^HOME FEV0.5/FVC% DETERMINATION",
"47652^HOME FEV0.75 DETERMINATION",
"47654^HOME FEV0.75/FVC% DETERMINATION",
"47656^HOME FEV1 DETERMINATION",
"47658^HOME FEV1/VC% DETERMINATION",
"47660^HOME FEV1/FVC% DETERMINATION",
"47662^HOME FEV1/PEF DETERMINATION",
"47664^HOME FEV3 DETERMINATION",
"47666^HOME FEV3/FVC% DETERMINATION",
"47668^HOME PEF DETERMINATION",
"47682^HOME FEF25-75% DETERMINATION",
"47670^HOME FEF25-75/FVC% DETERMINATION",
"47684^HOME FEF75-85% DETERMINATION",
"47686^HOME FEF0.2-1.2 DETERMINATION",
"47672^HOME FEF25% DETERMINATION",
"47674^HOME FEF50% DETERMINATION",
"47676^HOME FEF75% DETERMINATION",
"47678^HOME FMFT DETERMINATION",
```

FILE NO. A31572-A - 070050.0864

```
"47680^HOME FET DETERMINATION",
"47688^HOME MVV IND DETERMINATION",
"47690^HOME FIVC DETERMINATION",
"47692^HOME FIVC/FVC% DETERMINATION",
"47694^HOME PIF DETERMINATION",
"47696^HOME FIF25% DETERMINATION",
"47698^HOME FIF50% DETERMINATION",
"47700^HOME FIF75% DETERMINATION",
"47702^HOME FIF50/FEF50% DETERMINATION",
"47704^HOME FEV CURVE DETERMINATION",
"47706^HOME FIV CURVE DETERMINATION",
"47708^HOME SYNDROMAL INTERPRETATION DETERMINATION",
"47710^HOME FVC PREDICTED VALUE",
"47712^HOME FEV0.5 PREDICTED VALUE",
"47714^HOME FEV0.5/FVC% PREDICTED VALUE",
"47716^HOME FEV0.75 PREDICTED VALUE",
"47718^HOME FEV0.75/FVC% PREDICTED VALUE",
"47720^HOME FEV1 PREDICTED VALUE",
"47722^HOME FEV1/VC% PREDICTED VALUE",
"47724^HOME FEV1/FVC% PREDICTED VALUE",
"47726^HOME FEV1/PEF PREDICTED VALUE",
"47728^HOME FEV3 PREDICTED VALUE",
"47730^HOME FEV3/FVC% PREDICTED VALUE",
"47732^HOME PEF PREDICTED VALUE",
"47734^HOME FEF25-75% PREDICTED VALUE",
"47736^HOME FEF25-75/FVC% PREDICTED VALUE",
"47738^HOME FEF75-85% PREDICTED VALUE",
"47740^HOME FEF0.2-1.2 PREDICTED VALUE",
"47742^HOME FEF25% PREDICTED VALUE",
"47744^HOME FEF50% PREDICTED VALUE",
"47746^HOME FEF75% PREDICTED VALUE",
"47748^HOME FMFT PREDICTED VALUE",
"47750^HOME FET PREDICTED VALUE",
"47752^HOME MVV IND PREDICTED VALUE",
"47754^HOME FIVC PREDICTED VALUE",
"47756^HOME FIVC/FVC% PREDICTED VALUE",
"47758^HOME PIF PREDICTED VALUE",
"47760^HOME FIF25% PREDICTED VALUE",
"47762^HOME FIF50% PREDICTED VALUE",
"47764^HOME FIF75% PREDICTED VALUE",
```

FILE NO. A31572-A - 070050.0864

```
"47766^HOME FIF50/FEF50% PREDICTED VALUE",
"47768^HOME PERCENTAGE FVC OF PREDICTED VALUE",
"47770^HOME PERCENTAGE FEV0.5 OF PREDICTED VALUE",
"47772^HOME PERCENTAGE FEV0.5/FVC% OF PREDICTED VALUE",
"47774^HOME PERCENTAGE FEV0.75 OF PREDICTED VALUE",
"47776^HOME PERCENTAGE FEV0.75/FVC% OF PREDICTED VALUE",
"47778^HOME PERCENTAGE FEV1 OF PREDICTED VALUE",
"47780^HOME PERCENTAGE FEV1/VC% OF PREDICTED VALUE",
"47782^HOME PERCENTAGE FEV1/FVC% OF PREDICTED VALUE",
"47784^HOME PERCENTAGE FEV1/PEF OF PREDICTED VALUE",
"47786^HOME PERCENTAGE FEV3 OF PREDICTED VALUE",
"47788^HOME PERCENTAGE FEV3/FVC% OF PREDICTED VALUE",
"47790^HOME PERCENTAGE PEF OF PREDICTED VALUE",
"47792^HOME PERCENTAGE FEF25-75% OF PREDICTED VALUE",
"47794^PERCENTAGE HOME FEF25-75/FVC% OF PREDICTED VALUE",
"47796^PERCENTAGE HOME FEF75-85% OF PREDICTED VALUE",
"47798^HOME PERCENTAGE FEF0.2-1.2 OF PREDICTED VALUE",
"47800^HOME PERCENTAGE FEF25% OF PREDICTED VALUE",
"47802^HOME PERCENTAGE FEF50% OF PREDICTED VALUE",
"47804^HOME PERCENTAGE FEF75% OF PREDICTED VALUE",
"47806^HOME PERCENTAGE FMFT OF PREDICTED VALUE",
"47808^HOME PERCENTAGE FET OF PREDICTED VALUE",
"47810^HOME PERCENTAGE MVV IND OF PREDICTED VALUE",
"47812^HOME PERCENTAGE FIVC OF PREDICTED VALUE",
"47814^HOME PERCENTAGE FIVC/FVC% OF PREDICTED VALUE",
"47816^HOME PERCENTAGE PIF OF PREDICTED VALUE",
"47818^HOME PERCENTAGE FIF25% OF PREDICTED VALUE",
"47820^HOME PERCENTAGE FIF50% OF PREDICTED VALUE",
"47822^HOME PERCENTAGE FIF75% OF PREDICTED VALUE",
"47824^HOME PERCENTAGE FIF50/FEF50% OF PREDICTED VALUE",
"47826^HOME TEST VARIABILITY",
"47828^HOME METHOD OF PREDICTED VALUE CALCULATION",
"47830^HOME NUMBER OF TEST ATTEMPTS",
"47832^HOME TESTING DEVICE",
"49893^TECHNICAL NOTES OF HOME SPIROMETRY",
"49889^HOME MORNING SCORE",
"49891^HOME EVENING SCORE"};

printf("Content-type: text/html%c%c",10,10);
```

FILE NO. A31572-A - 070050.0864

```
if(strcmp(getenv("REQUEST_METHOD"),"POST")) {
    printf("This script should be referenced with a METHOD of POST.\n");
    printf("If you don't understand this, see this ");
    printf("<A HREF=\"http://www.ncsa.uiuc.edu/SDG/Software/Mosaic/Docs/fill-out-forms/overview.html\">forms overview</A>.%c",10);
    exit(1);
}
if(strcmp(getenv("CONTENT_TYPE"),"application/x-www-form-urlencoded")) {
    printf("This script can only be used to decode form results. \n");
    exit(1);
}
cl = atoi(getenv("CONTENT_LENGTH"));
for(x=0;cl && (!feof(stdin));x++) {
    m=x;
    entries[x].val = fmakeword(stdin,'&',&cl);
    plustospace(entries[x].val);
    unescape_url(entries[x].val);
    entries[x].name = makeword(entries[x].val,'=');
} printf("<H1>Pulmonary Function Testing</H1>"); /*
printf("You submitted the following name/value pairs:<p>%c",10);
printf("<ul>%c",10);

printf("<BR>m=%d<BR>",m);
printf("cl=%d<BR>",cl);
    for(x=0; x <= m; x++){
        printf("<li> <code>%s = %s</code>%c",entries[x].name,
            entries[x].val,10);
    }
    printf("</ul>%c",10);
    printf("\n<B>This is the end</B>");
*/ if (m==0) {
    printf("<B>Please choose the test</B>\n"); exit(0);
}
strcpy(MRN,entries[0].val);
```

FILE NO. A31572-A - 070050.0864

```
im = gdImageCreate(195, 500); /*180*/
black = gdImageColorAllocate(im, 0, 0, 0);
white = gdImageColorAllocate(im, 255, 255, 255);
red   = gdImageColorAllocate(im, 255, 0, 0);
/*blue*/clr[0] = gdImageColorAllocate(im, 0, 0, 255);
/*blue*/clr[1] = gdImageColorAllocate(im, 0, 255, 0);
/*blue*/clr[2] = gdImageColorAllocate(im, 0, 255, 255);
/*blue*/clr[3] = gdImageColorAllocate(im, 255, 0, 255);
/*blue*/clr[4] = gdImageColorAllocate(im, 255, 255, 0);
/*blue*/clr[5] = gdImageColorAllocate(im, 100, 255, 255);
/*blue*/clr[6] = gdImageColorAllocate(im, 255, 100, 255);
/*blue*/clr[7] = gdImageColorAllocate(im, 255, 255, 100);
gdImageLine(im,25,250,170,250,red);/*X*/ gdImageLine(im,25,460,25,40,red);/*Y*/
gdImageString(im,gdFontSmall, 25, 25,"F[l/s]",red);
gdImageString(im,gdFontSmall,160,235,"V[l]", red);
for (i=1;i<15;i++) {sprintf(str,"%3d",i);
          gdImageLine(im,23,250-i*15,27,250-i*15,red);
          gdImageString(im,gdFontSmall,3,250-i*15-6,str,red);
          gdImageLine(im,23,250+i*15,27,250+i*15,red);
          gdImageString(im,gdFontSmall,3,250+i*15-6,str,red);}
for (i=1;i<7;i++) {sprintf(str,"%d",i);
          gdImageLine(im,25+24*i,250-2,25+24*i,250+2,red);
          gdImageString(im,gdFontSmall,25+24*i-3,250+5,str,red);}

/* process the msg   */
strcpy(AccssN,entries[m].val);
test_hl7(msg,AccssN);

convGRdt(msg,s,"47704^^L!0!");
for (i=0;i<144;i++) MX[i]=0;
for (i=0;i<144;i++) {if ((i>1)&&(s[i]=='#')) break; MX[i]=s[i]-35; }
for (i=0;i<144;i++) gdImageLine(im,i+26,250-MX[i],i+1+26,250-MX[i+1],red);
for (i=0;i<144;i++) MX0[i]=MX[i];

convGRdt(msg,s,"47706^^L!0!");
for (i=0;i<144;i++) MX[i]=s[i]-35;
for (x=143;x>0;x--) if (MX[x]>0) break; if (x==143) x--;
for (i=0;i<x+1;i++) gdImageLine(im,i+26,250+MX[i],i+1+26,250+MX[i+1],red);
for (i=0;i<144;i++) MI0[i]=MX[i];
```

FILE NO. A31572-A - 070050.0864

```
CheckFls(s,AccssN);
out = fopen(s,"wb"); gdImageGif(im, out); fclose(out);
printf(
"<IMG SRC=\"http://www.cpmc.columbia.edu/tmp/%s\" ALIGN=left>\n",s+28);

PtData(msg);

printf("<TABLE BORDER>\n");
printf("<TR><TH>Index</TH><TH>Pred</TH><TH>Meas</TH><TH>%</TH></
TR>\n");
c=msg; c=gettxt(c,s,"OBX!5!");
for (i=0;i<29;i++) {
 printf("<TR><TH ALIGN=left>\n"); memcpy(s0,parHL7[i],5); s0[5]='\0';
 printf("<FORM METHOD=\"POST\" ACTION=\"trendpft.cgi\">\n");
 printf("<INPUT TYPE=\"hidden\" NAME=\"MRN\"    VALUE=\"%s\">",MRN);
 printf("<INPUT TYPE=\"hidden\" NAME=\"medcode\" VALUE=\"%s\">",s0);
 printf("<INPUT TYPE=\"submit\" VALUE=\"%02d\">",i+1);
 printf("%s</TH></FORM>\n",parnam[i]);
 for (cl=0;cl<3;cl++) {
  c=gettxt(c,s,"^^L!0!"); parval[cl][i]=atoff(s);
  if (parval[cl][i]<=0) strcpy(s,"---");
  printf("<TD ALIGN=right>%s</TD>",s); }
}
printf("</TABLE>\n");

Score(msg); PtMsg(msg);

for (z=m-1;z>=1;z--) { printf("<CENTER><P><IMG SRC=\"blumar.gif\"></P></CENTER>");

strcpy(AccssN,entries[z].val); test_hl7(msg,AccssN);

convGRdt(msg,s,"47704^^L!0!");
 for (i=0;i<144;i++) MX[i]=0;
 for (i=0;i<144;i++) {if ((i>1)&&(s[i]=='#')) break; MX[i]=s[i]-35; }
 for (i=0;i<144;i++) {
   if ((i>1)&&(MX[i]==0)) break; cl=m-1-z; if (cl>7) cl=7;
   gdImageLine(im,i+26,250-MX[i],i+1+26,250-MX[i+1],clr[cl]); }
```

FILE NO. A31572-A - 070050.0864

```
convGRdt(msg,s,"47706^^L!0!");
for (i=0;i<144;i++) MX[i]=s[i]-35;
for (x=143;x>0;x--) if (MX[x]>0) break; if (x==143) x--;
if (x>10) for (i=0;i<x+1;i++)
  gdImageLine(im,i+26,250+MX[i],i+1+26,250+MX[i+1],clr[cl]);

CheckFls(s,AccssN);
out = fopen(s,"wb"); gdImageGif(im, out); fclose(out);
printf(
"<IMG SRC=\"http://www.cpmc.columbia.edu/tmp/%s\" ALIGN=left>\n",s+28);

PtData(msg);

printf("<TABLE BORDER>\n");
printf("<TR><TH>Index</TH><TH>Pred</TH><TH>Meas</TH><TH>%</TH>\n"
);
printf("<TH>Meas</TH><TH>%</TH><TH>%</TH></TR>\n");
c=msg; c=gettxt(c,s,"OBX!5!");
for (i=0;i<29;i++) {
  printf("<TR><TH ALIGN=left>\n"); memcpy(s0,parHL7[i],5); s0[5]='\0';
  printf("<FORM METHOD=\"POST\" ACTION=\"trendpft.cgi\">\n");
  printf("<INPUT TYPE=\"hidden\" NAME=\"MRN\"   VALUE=\"%s\">",MRN);
  printf("<INPUT TYPE=\"hidden\" NAME=\"medcode\" VALUE=\"%s\">",s0);
  printf("<INPUT TYPE=\"submit\" VALUE=\"%02d\">",i+1);
  printf("%s</TH></FORM>\n",parnam[i]);
  for (cl=0;cl<3;cl++) {
    if (parval[cl][i]<=0) strcpy(s,"---");
      else if (cl==2) sprintf(s,"%6.0f",parval[cl][i]);
      else sprintf(s,"%6.2f",parval[cl][i]);
    printf("<TD ALIGN=right>%s</TD>",s); }
  c=gettxt(c,s,"^^L!0!");
  c=gettxt(c,s,"^^L!0!"); val=atoff(s); if (val<=0) strcpy(s,"---");
  printf("<TD ALIGN=right>%s</TD>",s);
  c=gettxt(c,s,"^^L!0!"); if (s[0]=='0') strcpy(s,"---");
  printf("<TD ALIGN=right>%s</TD>",s);
  if ((parval[1][i]<=0)||(val<=0)) strcpy(s,"---");
    else sprintf(s,"%6.0f",(val/parval[1][i])*100);
  printf("<TD ALIGN=right>%s</TD></TR>\n",s);
}
```

FILE NO. A31572-A - 070050.0864

```
printf("</TABLE>\n");

Score(msg); PtMsg(msg);

} gdImageDestroy(im);

/*clean some memory*/
  for(x=0;x <= m; x++){
    free(entries[x].name);
    free(entries[x].val);
  }
} void getword(char *word, char *line, char stop) {
  int x = 0,y;

for(x=0;((line[x]) && (line[x] != stop));x++)
     word[x] = line[x];

word[x] = '\0';
  if(line[x]) ++x;
  y=0;

while(line[y++] = line[x++]);
} char *makeword(char *line, char stop) {
  int x = 0,y;
  char *word = (char *) malloc(sizeof(char) * (strlen(line) + 1));

for(x=0;((line[x]) && (line[x] != stop));x++)
     word[x] = line[x];

word[x] = '\0';
  if(line[x]) ++x;
  y=0;
```

FILE NO. A31572-A - 070050.0864

```
    while(line[y++] = line[x++]);
    return word;
}
char *fmakeword(FILE *f, char stop, int *cl) {
    int wsize;
    char *word;
    int ll;

wsize = 102400;
    ll=0;
    word = (char *) malloc(sizeof(char) * (wsize + 1));

while(1) {
        word[ll] = (char)fgetc(f);
        if(ll==wsize) {
            word[ll+1] = '\0';
            wsize+=102400;
            word = (char *)realloc(word,sizeof(char)*(wsize+1));
        }
        --(*cl);
        if((word[ll] == stop) || (feof(f)) || (!(*cl))) {
            if(word[ll] != stop) ll++;
            word[ll] = '\0';
            return word;
        }
        ++ll;
    }
} char x2c(char *what) {
    register char digit;

digit = (what[0] >= 'A' ? ((what[0] & 0xdf) - 'A')+10 : (what[0] - '0'));
    digit *= 16;
    digit += (what[1] >= 'A' ? ((what[1] & 0xdf) - 'A')+10 : (what[1] - '0'));
    return(digit);
} void unescape_url(char *url) {
```

FILE NO. A31572-A - 070050.0864

```
    register int x,y;

for(x=0,y=0;url[y];++x,++y) {
        if((url[x] = url[y]) == '%') {
            url[x] = x2c(&url[y+1]);
            y+=2;
        }
    }
    url[x] = '\0';
} void plustospace(char *str) {
    register int x;

for(x=0;str[x];x++) if(str[x] == '+') str[x] = ' ';
} int rind(char *s, char c) {
    register int x;
    for(x=strlen(s) - 1;x != -1; x--)
        if(s[x] == c) return x;
    return -1;
} int getline(char *s, int n, FILE *f) {
    register int i=0;

while(1) {
        s[i] = (char)fgetc(f);

if(s[i] == CR)
            s[i] = fgetc(f);

if((s[i] == 0x4) || (s[i] == LF) || (i == (n-1))) {
            s[i] = '\0';
            return (feof(f) ? 1 : 0);
        }
        ++i;
    }
}
```

FILE NO. A31572-A - 070050.0864

```
void send_fd(FILE *f, FILE *fd)
{
  int num_chars=0;
  char c;

while (1) {
    c = fgetc(f);
    if(feof(f))
      return;
    fputc(c,fd);
  }
}
/*==================================================*/ void CheckFls(char *flnm, char *Acs)
{
int i;
FILE *f;
char fn[256];

sprintf(fn,"/localmisc/httpd/htdocs/tmp/%s.gif",Acs); i=0;
while ((f=fopen(fn,"r"))!=NULL) {
  fclose(f); sprintf(fn,"/localmisc/httpd/htdocs/tmp/%s%d.gif",Acs,i++);}
memccpy(flnm,fn,'\0',256);
} void convGRdt(char *c, char *s, char *hl7code)
{
char *c1;
c=gettxt(c,s,hl7code);
while ((c1=strstr(s,"\\S\\"))!=NULL)
    {*c1++='^'; *c1++='\0'; c1++; strcat(s,c1);}
while ((c1=strstr(s,"\\R\\"))!=NULL)
    {*c1++='~'; *c1++='\0'; c1++; strcat(s,c1);}
while ((c1=strstr(s,"\\E\\"))!=NULL)
    {*c1++='&'; *c1++='\0'; c1++; strcat(s,c1);}
} void PtData(char *c)
{
```

FILE NO. A31572-A - 070050.0864

```
char s[256],s0[256],s1[16],s2[16],s3[16],s4[32],*pnt;
pnt=c;

printf(
"<B><U>MRN:</U></B> %s<BR>\n",MRN);

c=gettxt(pnt,s,"47704^^L!0!"); sscanf(s,"%s%s%s%s%s",s0,s1,s2,s3,s4);
printf("<B><U>Age:</U></B> %s <B><U>Height:</U></B> %s ins ",s1,s2);
printf("<B><U>Sex:</U></B> %s<BR><B><U>Ethnic Origin:</U></B>
%s<BR>\n",s3,s4);
c=pnt;

c=gettxt(c,s,"47639^^L!!!"); strncpy(s0,s+4,2); s0[2]='\0';
printf("<B><U>Test Date:</U></B> %s/",s0);
strncpy(s0,s+6,2); s0[2]='\0'; printf("%s/",s0);
strncpy(s0,s,4); s0[4]='\0'; printf("%s    ",s0);
strncpy(s0,s+8,2); s0[2]='\0'; printf("<BR><B><U>Time:</U></B> %s:",s0);
strncpy(s0,s+10,2); s0[2]='\0'; printf("%s:",s0);
strncpy(s0,s+12,2); s0[2]='\0'; printf("%s<BR>\n",s0);

printf("<B><U>Test Quality Information:</U></B><BR>");
c=gettxt(c,s,"47826^^L!0!"); printf("<B><I>Variability - </I></B> %s<BR>\n",s);
c=gettxt(c,s,"47830^^L!0!");printf("<B><I>Number of tests:</I></B> %s<BR>\n",s);
c=gettxt(c,s,"47828^^L!0!"); printf("%s<BR>\n",s);
c=gettxt(c,s,"47708^^L!0!");
printf("<B><U>Interpretation of test results:</U></B><BR>\n%s<BR><P><HR>\n",s);
} char *gettxt(char *msgpnt,char *txtdat,char *ptrn)
{
int i;
msgpnt=strstr(msgpnt,ptrn); msgpnt+=strlen(ptrn);
i=0; while (*msgpnt!='!') txtdat[i++]=*msgpnt++; txtdat[i]='\0';
return(msgpnt);
} void test_hl7(char *data,char *AcsN)
{
int yr,mt,dy,hr,mn,sc;
int a,i,k;
```

FILE NO. A31572-A - 070050.0864

```
char
qryLn1_1[]="MSH!^~\\&!tst!cucis!cis.qservice!cicsl9.phis!19950125120000!!QRY!1995
0125120000!D!2.1!\"\"!";
char qryLn2_1[]="\rQRD!19950125120000!R!I!finkelj!!!0!"; /*3131313*/
char qryLn2_2[]="!RES!*!*!B";
char
qryLn3_1[]="\rQRF!*!19921104000000!19981231110700!SERVICE~*~*~*!95~57~55~
*~0158";
char qryLn3_2[]="~A~UR~ ~*~*~*~*~158";
char       outmsg[32755],s[512];
unsigned short   outlength;
char       qry[1024]="",tmp_qry[10024]="";
FILE *f;
char svc[]="cis.qservice@cicst2.phis%ciscomtab";

sprintf(qry,"%s%s%s%s%s%s%s",
      qryLn1_1,qryLn2_1,MRN,qryLn2_2,qryLn3_1,AcsN,qryLn3_2);
  i=k=0;
  while(!k&&i<5) {
    k=0;
    outlength=32754;
    sprintf(tmp_qry,"%s",qry); sprintf(s,"%s","");
    k=hl7sap(s,tmp_qry,outmsg,&outlength);
    outmsg[outlength]='\0';
    if(!k) i++;
  }
  if(!k&&i==5) {
    fprintf(stderr,"Failed on HL7SAP\n");
  }
for (i=0; i<strlen(outmsg);i++) {
  if(outmsg[i]=='\r') outmsg[i]='\n';
}
strcpy(data,outmsg);
} void Score(char *msgpnt)
{
char *pnt, s[256], s0[8];
int sc[10],i;
```

FILE NO. A31572-A - 070050.0864

```
char sc4[4][10]={"none","mild","moderate","severe"};
char am4[4][30]={"as usual","slightly increased",
        "significantly increased","maximal"};
char morSc[3][36]={
  "Disturbance of the sleep by asthma",
  "Number of awakening by asthma",
  "Nightime reliever use"};
char eveSc[10][36]={
  "Wheeze",
  "Cough",
  "Sputum production",
  "Chest tightness",
  "Shortness of breath",
  "Limitation of physical activity",
  "Over-all use of asthma medications",
  "Exposure to asthma triggers",
  "Over-all estimate of asthma",
  "Daytime reliever use"};

pnt=msgpnt;
if (strstr(pnt,"49889^^L")!=NULL) {
 pnt=gettxt(msgpnt,s,"49889^^L!0!"); if (*s=='G') {
   sscanf(s,"%s%d%d%d",s0,&sc[0],&sc[1],&sc[2]); sc[0]=sc[0]-48;
   puts("<CENTER><TABLE BORDER>");
   puts("<CAPTION><FONT COLOR=\"#0000FF\">Asthma
Diary</FONT></CAPTION>");
   puts("<TR><TH>Symptom</TH><TH>Score</TH><TH>Meaning</TH></TR>");
   for (i=0;i<3;i++) {
     switch (i) {
        case 0: strcpy(s,sc4[sc[i]]); break;
        case 1: strcpy(s,"night awakening"); break;
        case 2: strcpy(s,"inhaler puffs"); break;
     }
     printf(
     "<TR><TH ALIGN=left>%s</TH><TD
ALIGN=center>%d</TD><TD>%s</TD>\n",
     morSc[i],sc[i],s);
   }
   puts("</TABLE></CENTER>");
 }
```

- 106 -

FILE NO. A31572-A - 070050.0864

```
}
else if (strstr(pnt,"49891^^L")!=NULL) {
  pnt=gettxt(msgpnt,s,"49891^^L!0!"); if (*s=='G') {
    sscanf(s,"%s%d%d%d%d%d%d%d%d%d%d",s0,
      &sc[0],&sc[1],&sc[2],&sc[3],&sc[4],&sc[5],&sc[6],&sc[7],&sc[8],&sc[9]);
    for (i=0;i<9;i++) sc[i]=sc[i]-48;
    puts("<CENTER><TABLE BORDER>");
    puts("<CAPTION><FONT COLOR=\"#0000FF\">Asthma
Diary</FONT></CAPTION>");
    puts("<TR><TH>Symptom</TH><TH>Score</TH><TH>Meaning</TH></TR>");
    for (i=0;i<10;i++) {
      if (i==6) strcpy(s,am4[sc[i]]);
        else if (i==9) strcpy(s,"inhaler puffs"); else strcpy(s,sc4[sc[i]]);
      printf(
      "<TR><TH ALIGN=left>%s</TH><TD
ALIGN=center>%d</TD><TD>%s</TD>\n",
      eveSc[i],sc[i],s);
    }
    puts("</TABLE></CENTER>");
  }
}

} void PtMsg(char *hl7msg)
{
char *pnt,*c1,*c2,s[512];
pnt=hl7msg; if (strstr(pnt,"49893^^L")==NULL) return;
pnt=gettxt(hl7msg,s,"49893^^L!0!");
if (((c1=strstr(s,"{*"))==NULL)||(strstr(s,"{**")!=NULL)) return;
c2=strstr(s,"*}"); pnt=s; c1+=2; while (c1<c2) *pnt++=*c1++; *pnt='\0';
puts("<CENTER><FONT COLOR=\"#0000FF\">Message from the
patient</FONT><BR>");
puts(s); puts("</CENTER>");
}
```

FILE NO. A31572-A - 070050.0864

<u>trendpft</u>

```c
#include <stdio.h>
#include <stdlib.h>
include <sys/file.h>
#include <string.h>
#include <memory.h>
include <time.h> define MAX_ENTRIES 10000
define LF 10
define CR 13 typedef struct {
   char *name;
   char *val;
} entry;

char *makeword(char *line, char stop);
char *fmakeword(FILE *f, char stop, int *len);
char x2c(char *what);
void unescape_url(char *url);
void plustospace(char *str);

void test_hl7(char *m);
char *gettxt(char *msgpnt,char *txtdat,char *ptrn);
char *parDim(int pnum);

char MRN[10],MED[8];

main(int argc, char *argv[]) {
   entry entries[MAX_ENTRIES];
   register int x,m=0;
   int cl;
int i,z,N;
int MX[144],MX0[144],MI0[144],clr[10];
float parval[3][29],val;
FILE *out;
char s[256],s0[64],AccssN[32];
char msg[32755];
```

FILE NO. A31572-A - 070050.0864

```
char *c2,*c1,*c=msg;
int black,white,red,blue;
char str[4];
struct tm Tstr;
time_t ts[3000];
char par[3000][10];
char parnam[29][20]={
    "FVC","FEV.5","FEV.5/FVC%","FEV.75","FEV.75/FVC%","FEV1", "FEV1/VC%","FEV1/FVC%","FEV1/PEF","FEV3","FEV3/FVC%","PEF"
,
    "FEF25-75%","FEF25-75/FVC","FEF75-85%","FEF.2-1.2","FEF25%", "FEF50%","FEF75%","FMFT","FET","MVVind","FIVC","FIVC/FVC%",
    "PIF","FIF25%","FIF50%","FIF75%","FIF50/FEF50%"};

char parHL7[97][55]={
"47646^HOME FVC DETERMINATION",
"47648^HOME FEV0.5 DETERMINATION",
"47650^HOME FEV0.5/FVC% DETERMINATION",
"47652^HOME FEV0.75 DETERMINATION",
"47654^HOME FEV0.75/FVC% DETERMINATION",
"47656^HOME FEV1 DETERMINATION",
"47658^HOME FEV1/VC% DETERMINATION",
"47660^HOME FEV1/FVC% DETERMINATION",
"47662^HOME FEV1/PEF DETERMINATION",
"47664^HOME FEV3 DETERMINATION",
"47666^HOME FEV3/FVC% DETERMINATION",
"47668^HOME PEF DETERMINATION",
"47682^HOME FEF25-75% DETERMINATION",
"47670^HOME FEF25-75/FVC% DETERMINATION",
"47684^HOME FEF75-85% DETERMINATION",
"47686^HOME FEF0.2-1.2 DETERMINATION",
"47672^HOME FEF25% DETERMINATION",
"47674^HOME FEF50% DETERMINATION",
"47676^HOME FEF75% DETERMINATION",
"47678^HOME FMFT DETERMINATION",
"47680^HOME FET DETERMINATION",
"47688^HOME MVV IND DETERMINATION",
"47690^HOME FIVC DETERMINATION",
```

FILE NO. A31572-A - 070050.0864

"47692^HOME FIVC/FVC% DETERMINATION",
"47694^HOME PIF DETERMINATION",
"47696^HOME FIF25% DETERMINATION",
"47698^HOME FIF50% DETERMINATION",
"47700^HOME FIF75% DETERMINATION",
"47702^HOME FIF50/FEF50% DETERMINATION",
"47704^HOME FEV CURVE DETERMINATION",
"47706^HOME FIV CURVE DETERMINATION",
"47708^HOME SYNDROMAL INTERPRETATION DETERMINATION",
"47710^HOME FVC PREDICTED VALUE",
"47712^HOME FEV0.5 PREDICTED VALUE",
"47714^HOME FEV0.5/FVC% PREDICTED VALUE",
"47716^HOME FEV0.75 PREDICTED VALUE",
"47718^HOME FEV0.75/FVC% PREDICTED VALUE",
"47720^HOME FEV1 PREDICTED VALUE",
"47722^HOME FEV1/VC% PREDICTED VALUE",
"47724^HOME FEV1/FVC% PREDICTED VALUE",
"47726^HOME FEV1/PEF PREDICTED VALUE",
"47728^HOME FEV3 PREDICTED VALUE",
"47730^HOME FEV3/FVC% PREDICTED VALUE",
"47732^HOME PEF PREDICTED VALUE",
"47734^HOME FEF25-75% PREDICTED VALUE",
"47736^HOME FEF25-75/FVC% PREDICTED VALUE",
"47738^HOME FEF75-85% PREDICTED VALUE",
"47740^HOME FEF0.2-1.2 PREDICTED VALUE",
"47742^HOME FEF25% PREDICTED VALUE",
"47744^HOME FEF50% PREDICTED VALUE",
"47746^HOME FEF75% PREDICTED VALUE",
"47748^HOME FMFT PREDICTED VALUE",
"47750^HOME FET PREDICTED VALUE",
"47752^HOME MVV IND PREDICTED VALUE",
"47754^HOME FIVC PREDICTED VALUE",
"47756^HOME FIVC/FVC% PREDICTED VALUE",
"47758^HOME PIF PREDICTED VALUE",
"47760^HOME FIF25% PREDICTED VALUE",
"47762^HOME FIF50% PREDICTED VALUE",
"47764^HOME FIF75% PREDICTED VALUE",
"47766^HOME FIF50/FEF50% PREDICTED VALUE",
"47768^HOME PERCENTAGE FVC OF PREDICTED VALUE",
"47770^HOME PERCENTAGE FEV0.5 OF PREDICTED VALUE",

FILE NO. A31572-A - 070050.0864

"47772^HOME PERCENTAGE FEV0.5/FVC% OF PREDICTED VALUE",
"47774^HOME PERCENTAGE FEV0.75 OF PREDICTED VALUE",
"47776^HOME PERCENTAGE FEV0.75/FVC% OF PREDICTED VALUE",
"47778^HOME PERCENTAGE FEV1 OF PREDICTED VALUE",
"47780^HOME PERCENTAGE FEV1/VC% OF PREDICTED VALUE",
"47782^HOME PERCENTAGE FEV1/FVC% OF PREDICTED VALUE",
"47784^HOME PERCENTAGE FEV1/PEF OF PREDICTED VALUE",
"47786^HOME PERCENTAGE FEV3 OF PREDICTED VALUE",
"47788^HOME PERCENTAGE FEV3/FVC% OF PREDICTED VALUE",
"47790^HOME PERCENTAGE PEF OF PREDICTED VALUE",
"47792^HOME PERCENTAGE FEF25-75% OF PREDICTED VALUE",
"47794^PERCENTAGE HOME FEF25-75/FVC% OF PREDICTED VALUE",
"47796^PERCENTAGE HOME FEF75-85% OF PREDICTED VALUE",
"47798^HOME PERCENTAGE FEF0.2-1.2 OF PREDICTED VALUE",
"47800^HOME PERCENTAGE FEF25% OF PREDICTED VALUE",
"47802^HOME PERCENTAGE FEF50% OF PREDICTED VALUE",
"47804^HOME PERCENTAGE FEF75% OF PREDICTED VALUE",
"47806^HOME PERCENTAGE FMFT OF PREDICTED VALUE",
"47808^HOME PERCENTAGE FET OF PREDICTED VALUE",
"47810^HOME PERCENTAGE MVV IND OF PREDICTED VALUE",
"47812^HOME PERCENTAGE FIVC OF PREDICTED VALUE",
"47814^HOME PERCENTAGE FIVC/FVC% OF PREDICTED VALUE",
"47816^HOME PERCENTAGE PIF OF PREDICTED VALUE",
"47818^HOME PERCENTAGE FIF25% OF PREDICTED VALUE",
"47820^HOME PERCENTAGE FIF50% OF PREDICTED VALUE",
"47822^HOME PERCENTAGE FIF75% OF PREDICTED VALUE",
"47824^HOME PERCENTAGE FIF50/FEF50% OF PREDICTED VALUE",
"47826^HOME TEST VARIABILITY",
"47828^HOME METHOD OF PREDICTED VALUE CALCULATION",
"47830^HOME NUMBER OF TEST ATTEMPTS",
"47832^HOME TESTING DEVICE",
"49893^TECHNICAL NOTES OF HOME SPIROMETRY",
"49889^HOME MORNING SCORE",
"49891^HOME EVENING SCORE"};

```
    printf("Content-type: text/html%c%c",10,10);

if(strcmp(getenv("REQUEST_METHOD"),"POST")) {
        printf("This script should be referenced with a METHOD of POST.\n");
        printf("If you don't understand this, see this ");
```

FILE NO. A31572-A - 070050.0864

```
    printf("<A
HREF=\"http://www.ncsa.uiuc.edu/SDG/Software/Mosaic/Docs/fill-out-forms/overview.h
tml\">forms overview</A>.%c",10);
    exit(1);
}
if(strcmp(getenv("CONTENT_TYPE"),"application/x-www-form-urlencoded")) {
    printf("This script can only be used to decode form results. \n");
    exit(1);
}
cl = atoi(getenv("CONTENT_LENGTH"));
for(x=0;cl && (!feof(stdin));x++) {
    m=x;
    entries[x].val = fmakeword(stdin,'&',&cl);
    plustospace(entries[x].val);
    unescape_url(entries[x].val);
    entries[x].name = makeword(entries[x].val,'=');
} printf("<H1>Pulmonary Function Testing</H1>"); /*
    printf("You submitted the following name/value pairs:<p>%c",10);
    printf("<ul>%c",10);

printf("<BR>m=%d<BR>",m);
printf("cl=%d<BR>",cl);
    for(x=0; x <= m; x++){
        printf("<li> <code>%s = %s</code>%c",entries[x].name,
            entries[x].val,10);
    }
    printf("</ul>%c",10);
    printf("\n<B>This is the end</B>");
*/ if (m==0) {
    printf("<B>Please choose the test</B>\n"); exit(0);
}
strcpy(MRN,entries[0].val);
strcpy(MED,entries[1].val);

/*  get the data   */
```

FILE NO. A31572-A - 070050.0864

```
test_hl7(msg);
c=gettxt(msg,s,"TOTAL ROWS="); N=atoi(s);

puts("<HTML><HEAD><TITLE>CPMC2</TITLE></HEAD>");
puts("<BODY><H2>Forced Vital Capacity Test</H2>");
puts("<APPLET CODE=\"jclass/chart/JCChartApplet.class\" HEIGHT=300
WIDTH=400>");
i=0; while (strstr(parHL7[i],MED)==NULL) i++;
sscanf(parHL7[i],"%s%s%s",AccssN,s,s0); if (i==21) strcat(s,s0);
puts("<PARAM NAME=header.isShowing VALUE=\"true\">");
printf("<PARAM NAME=header.text VALUE=\"%s(%s) trend\">\n",s,parDim(i));
puts("<PARAM NAME=data VALUE=\"");
printf(" ARRAY \" 1 %d T\n",N);

/*
OBX!6!NM!47646^^L!0!4.19!LITER!!!
*/
c=msg; Tstr.tm_isdst=-1;
for (i=0;i<N;i++) {
  c=gettxt(c,s0,"47639^^L!!!");
  memcpy(s,s0,4); s[4]='\0'; Tstr.tm_year=atoi(s)-1900;
  memcpy(s,s0+4,2); s[2]='\0'; Tstr.tm_mon=atoi(s)-1;
  memcpy(s,s0+6,2); Tstr.tm_mday=atoi(s);
  memcpy(s,s0+8,2); Tstr.tm_hour=atoi(s);
  memcpy(s,s0+10,2); Tstr.tm_min=atoi(s);
  memcpy(s,s0+12,2); Tstr.tm_sec=atoi(s); ts[i]=mktime(&Tstr);
  c=strstr(c,"!NM!"); c1=c+15; c2=s; *c2++=*c1++;
  while (*c1!='!') *c2++=*c1++; *c2='\0'; c=c1; strcpy(par[i],s);
}
/*for (i=N-1;i<0;i--) printf(" %ld %s\n",ts[i],par[i]);*/
for (i=N-1;i>=0;i--) printf(" %d %s\n",N-i,par[i]);

puts("\">");
puts("</APPLET></BODY></HTML>");

/*clean some memory*/
  for(x=0;x <= m; x++){
    free(entries[x].name);
    free(entries[x].val);
  }
```

FILE NO. A31572-A - 070050.0864

```
} char *parDim(int pnum) { /*28/29*/
switch (pnum) {
case 0:
case 1:return("LITER"); break;
case 2:return("%"); break;
case 3:return("LITER"); break;
case 4:return("%"); break;
case 5:return("LITER"); break;
case 6:
case 7:return("%"); break;
case 8:return("MIN"); break;
case 9:return("LITER"); break;
case 10:return("%"); break;
case 11:return("LITER/MIN"); break;
case 12:return("LITER/SEC"); break;
case 13:return("%"); break;
case 14:
case 15:
case 16:
case 17:
case 18:return("LITER/SEC"); break;
case 19:
case 20:return("SEC"); break;
case 21:return("LITER/MIN"); break;
case 22:return("LITER"); break;
case 23:return("%"); break;
case 24:return("LITER/MIN"); break;
case 25:
case 26:
case 27:return("LITER/SEC"); break;
case 28:return("%");
}
} void getword(char *word, char *line, char stop) {
   int x = 0,y;
```

FILE NO. A31572-A - 070050.0864

```c
  for(x=0;((line[x]) && (line[x] != stop));x++)
     word[x] = line[x];

word[x] = '\0';
  if(line[x]) ++x;
  y=0;

while(line[y++] = line[x++]);
} char *makeword(char *line, char stop) {
  int x = 0,y;
  char *word = (char *) malloc(sizeof(char) * (strlen(line) + 1));

for(x=0;((line[x]) && (line[x] != stop));x++)
     word[x] = line[x];

word[x] = '\0';
  if(line[x]) ++x;
  y=0;

while(line[y++] = line[x++]);
  return word;
} char *fmakeword(FILE *f, char stop, int *cl) {
  int wsize;
  char *word;
  int ll;

wsize = 102400;
  ll=0;
  word = (char *) malloc(sizeof(char) * (wsize + 1));

while(1) {
     word[ll] = (char)fgetc(f);
     if(ll==wsize) {
        word[ll+1] = '\0';
        wsize+=102400;
        word = (char *)realloc(word,sizeof(char)*(wsize+1));
```

FILE NO. A31572-A - 070050.0864

```
      }
      --(*cl);
      if((word[ll] == stop) || (feof(f)) || (!(*cl))) {
        if(word[ll] != stop) ll++;
        word[ll] = '\0';
        return word;
      }
      ++ll;
    }
} char x2c(char *what) {
  register char digit;

digit = (what[0] >= 'A' ? ((what[0] & 0xdf) - 'A')+10 : (what[0] - '0'));
  digit *= 16;
  digit += (what[1] >= 'A' ? ((what[1] & 0xdf) - 'A')+10 : (what[1] - '0'));
  return(digit);
} void unescape_url(char *url) {
  register int x,y;

for(x=0,y=0;url[y];++x,++y) {
    if((url[x] = url[y]) == '%') {
      url[x] = x2c(&url[y+1]);
      y+=2;
    }
  }
  url[x] = '\0';
} void plustospace(char *str) {
  register int x;

for(x=0;str[x];x++) if(str[x] == '+') str[x] = ' ';
} int rind(char *s, char c) {
  register int x;
```

FILE NO. A31572-A - 070050.0864

```c
    for(x=strlen(s) - 1;x != -1; x--)
      if(s[x] == c) return x;
    return -1;
} int getline(char *s, int n, FILE *f) {
  register int i=0;

while(1) {
    s[i] = (char)fgetc(f);

if(s[i] == CR)
      s[i] = fgetc(f);

if((s[i] == 0x4) || (s[i] == LF) || (i == (n-1))) {
      s[i] = '\0';
      return (feof(f) ? 1 : 0);
    }
    ++i;
  }
} void send_fd(FILE *f, FILE *fd)
{
  int num_chars=0;
  char c;

while (1) {
    c = fgetc(f);
    if(feof(f))
      return;
    fputc(c,fd);
  }
}
/*===============================================================*/ char *gettxt(char *msgpnt,char *txtdat,char *ptrn)
{
int i;
msgpnt=strstr(msgpnt,ptrn); msgpnt+=strlen(ptrn);
```

- 117 -

FILE NO. A31572-A - 070050.0864

```c
i=0; while (*msgpnt!='!') txtdat[i++]=*msgpnt++; txtdat[i]='\0';
return(msgpnt);
} void test_hl7(char *data)
{
/*
MSH!^~\&!tst!cucis!cis.qservice!cicsl9.phis!19950125120000!!QRY!19950125120000!D
!2.1!""!
QRD!19950125120000!R!I!finkelj!!!0!3131313!RES!47646!*!C
QRF!*!19901104000000!19961231110700!SERVICE~*~*~*!95~57~55~*~~ ~UR~
~*~*~*~*~158
*/
int yr,mt,dy,hr,mn,sc;
int a,i,k;
char
qryLn1_1[]="MSH!^~\\&!tst!cucis!cis.qservice!cicsl9.phis!19950125120000!!QRY!1995
0125120000!D!2.1!\"\"!";
char qryLn2_1[]="\rQRD!19950125120000!R!I!finkelj!!!0!"; /*3131313*/
char qryLn2_2[]="!RES!"; /***/
char qryLn2_3[]="!*!C";
char
qryLn3_1[]="\rQRF!*!19921104000000!19981231110700!SERVICE~*~*~*!95~57~55~
*~~ ~UR~ ~*~*~*~*~158";
char        outmsg[32755],s[512];
unsigned short    outlength;
char        qry[1024]="",tmp_qry[10024]="";
FILE *f;
char svc[]="cis.qservice@cicst2.phis%ciscomtab";

sprintf(qry,"%s%s%s%s%s%s%s",
      qryLn1_1,qryLn2_1,MRN,qryLn2_2,MED,qryLn2_3,qryLn3_1);
  i=k=0;
  while(!k&&i<5) {
    k=0;
    outlength=32754;
    sprintf(tmp_qry,"%s",qry); sprintf(s,"%s","");
    k=hl7sap(s,tmp_qry,outmsg,&outlength);
    outmsg[outlength]='\0';
    if(!k) i++;
```

FILE NO. A31572-A - 070050.0864

```
    }
    if(!k&&i==5) {
        fprintf(stderr,"Failed on HL7SAP\n");
    }
    for (i=0; i<strlen(outmsg);i++) {
        if(outmsg[i]=='\r') outmsg[i]='\n';
    }
    strcpy(data,outmsg);
}
```

What is claimed is:

1. A system for monitoring asthma severity comprising:

a remotely located asthma monitoring station for administering a patient self-test to gather test data and relevant patient information indicative of asthmatic symptoms and conditions;

a remotely located diagnosis/evaluation station;

a central processing facility receiving said test data and patient information from said monitoring station, processing said test data to determine whether said test data is valid, analyzing valid test data to generate test results and an appropriate response message to said monitoring station, storing said test results in a central data repository, and disseminating said test results and response message in a timely manner as required to one or both of said monitoring station and diagnosis/evaluation station;

and selectable data links coupling said monitoring station, said central processing facility, and said diagnosis/evaluation station for providing real-time reciprocal exchange of said test data, said test results, said response message and said patient information between said monitoring station, said central processing facility and said diagnosis/evaluation station, and for allowing the display of one or more of said test data, said test results, said response message and said patient information at one or both of said monitoring station and said diagnosis/evaluation station.

2. The system according to claim 1, wherein said remotely located asthma monitoring station comprises:

a spirometer for performing a forced vitality capacity test;

a symptom diary for storing answers to questions regarding relevant patient information;

a computing device coupled to said spirometer for administering said forced vitality capacity test and for reciprocal data exchange with said central processing facility.

3. The system according to claim 2, wherein said remotely located diagnosis/evaluation station comprises a graphical user interface for displaying results from said forced vitality capacity test in graphical and tabular form.

4. The system according to claim 3, wherein said graphical user interface is an Internet Web browser.

5. The system according to claim 1, wherein said central processing facility comprises a feedback loop for automatically transmitting a request response message to said monitoring station when said test data is invalid, a confirmation message when test data is valid, and an alert message when valid test data is determined to be outside pre-determined alert limits.

6. The system according to claim 1, wherein one or more of said data links are provided via a wireless communication system.

7. The system according to claim 1, wherein one or more of said data links are provided via a landline communication system.

8. The system according to claim 1, wherein one or more of said data links are provided via the Internet.

9. The system according to claim 1, further comprising a plurality of remotely located asthma monitoring stations.

10. The system according to claim 1, further comprising a plurality of remotely located diagnosis/evaluation stations.

11. The system according to claim 1, further comprising at least one diagnosis/evaluation station located at said central processing facility.

12. The system according to claim 1, further comprising at distributed computer program for controlling said system for remotely monitoring asthma severity.

13. The system according to claim 1, comprising:

at least one remotely located computer usable medium;

at least one centrally located computer usable medium; and distributed computer readable program code means embodied in said remotely and centrally located computer usable media, said program code means comprising:

means for administering a self-test at a remotely located monitoring station to gather test data and relevant patient information indicative of asthmatic symptoms and conditions;

means for transmitting said test data and patient information from said monitoring station to a central processing facility;

means for processing said test data at said central facility network to determine whether said test data is valid;

means for analyzing valid test data at said central processing facility to generate test results and an appropriate response message;

means for storing said test results in a central data repository;

means for disseminating said test results and said response message in a timely manner as required to one or both of said monitoring station and a remotely located diagnosis/evaluation station; and means for displaying said test results, said response message and said patient information at one or both of said monitoring station and said diagnosis/evaluation station.

14. The system according to claim 1, further comprising test results previously stored in said central data repository for analyzing said test data received by said central processing facility from said monitoring station.

15. The system according to claim 1, further comprising test results previously stored in said central data repository for display at one or both of said monitoring station and said remotely located diagnosis/evaluation station.

16. A method for monitoring asthma severity comprising the steps of:

administering a self-test at a remotely located monitoring station to gather test data and relevant patient information indicative of asthmatic symptoms and conditions;

transmitting said test data and patient information from said monitoring station to a central processing facility;

processing said test data at said central processing facility to determine whether said test data is valid;

analyzing valid test data at said central processing facility to generate test results and an appropriate response message;

storing said test results in a central data repository;

disseminating said test results and said response message in a timely manner as required to one or both of said monitoring station and a remotely located diagnosis/evaluation station; and displaying said test results, said response message and said patient information at one or both of said monitoring station and said diagnosis/evaluation station.

17. The method according to claim 16, further comprising the step of generating an appropriate request response when said test data is determined to be invalid by said central processing facility.

18. The method according to claim 16, wherein said step of analyzing said test data comprises the step of analyzing previously stored test results.

19. The method according to claim 16, further comprising the step of displaying previously stored test results.

* * * * *